United States Patent
Kita et al.

(10) Patent No.: US 7,454,945 B1
(45) Date of Patent: Nov. 25, 2008

(54) MERCURY MONITORING SYSTEM AND CALIBRATION

(75) Inventors: Dieter Kita, Blackstone, MA (US); James H. Grassi, Westwood, MA (US); Jeffrey Socha, Berlin, MA (US); Bryan A. Marcotte, Blackstone, MA (US)

(73) Assignee: Thermo Electron, Inc., Waltham, MA (US)

( * ) Notice: Subject to any disclaimer, the term of this patent is extended or adjusted under 35 U.S.C. 154(b) by 174 days.

(21) Appl. No.: 11/529,766

(22) Filed: Sep. 27, 2006

Related U.S. Application Data

(63) Continuation-in-part of application No. 11/120,315, filed on May 5, 2005, and a continuation-in-part of application No. 11/120,317, filed on May 2, 2005, now Pat. No. 7,354,553, and a continuation-in-part of application No. 11/120,316, filed on May 2, 2005, and a continuation-in-part of application No. 11/120,182, filed on May 2, 2005.

(51) Int. Cl.
*G01N 21/93* (2006.01)

(52) U.S. Cl. ............... 73/1.03; 73/1.06; 73/1.07; 73/31.05; 422/83; 422/93; 436/81

(58) Field of Classification Search ............ 73/1.02, 73/1.03, 1.06, 1.07, 23.2, 23.31, 31.03, 31.05, 73/31.06, 31.07; 422/83, 93, 94, 98; 436/73, 436/81

See application file for complete search history.

(56) References Cited

U.S. PATENT DOCUMENTS

| | | | | |
|---|---|---|---|---|
| 4,698,314 A | * | 10/1987 | Tao | 436/171 |
| 5,733,786 A | * | 3/1998 | Green | 436/81 |
| 6,690,462 B2 | * | 2/2004 | Seltzer | 356/316 |
| 6,830,730 B2 | * | 12/2004 | Rhodes | 422/78 |
| 6,863,005 B2 | * | 3/2005 | Lanier et al. | 110/345 |
| 7,285,419 B2 | * | 10/2007 | Shade et al. | 436/81 |
| 7,341,667 B2 | * | 3/2008 | Kennard et al. | 210/688 |
| 7,368,289 B2 | * | 5/2008 | Baldwin et al. | 436/81 |
| 2003/0103206 A1 | * | 6/2003 | Seltzer | 356/316 |
| 2005/0061110 A1 | * | 3/2005 | Schaedlich et al. | 75/670 |

* cited by examiner

*Primary Examiner*—David A. Rogers
(74) *Attorney, Agent, or Firm*—Chapin IP Law, LLC

(57) ABSTRACT

A calibration assembly generates elemental mercury and oxidized mercury for calibrating components of a mercury monitoring system, including making necessary adjustments to efficiencies of a mercury compound converter and an elemental mercury detector. The calibrator generates an elemental mercury sample having a known elemental mercury concentration, $[Hg^0]_1$ and combines an oxidizing component with the elemental mercury sample, thereby producing a reduced concentration of elemental mercury $[Hg^0]_2$ within the sample. The calibrator measures the concentration of elemental mercury $[Hg^0]_2$ within the sample and calculates a difference between the known elemental mercury concentration, $[Hg^0]_1$ and the reduced concentration $[Hg^0]_2$. The difference between $[Hg^0]_1$ and $[Hg^0]_2$ is substantially equal to the concentration of oxidized mercury produced by the calibrator. The concentration of oxidized mercury can also be calculated as the difference between elemental mercury detected after passing a sample stream containing oxidized mercury through a channel which includes the converter and the reduced concentration $[Hg^0]_2$ detected after passing the sample stream through a channel which bypasses the converter. By providing oxidized mercury at calculated concentrations, the calibrator allows a user to calibrate continuous emission monitoring systems for accurate response to both elemental mercury and oxidized mercury.

34 Claims, 16 Drawing Sheets

MERCURY MONITORING SYSTEM AND CALIBRATION

RELATED APPLICATIONS

This patent application is a Continuation in Part of:

i) U.S. patent application Ser. No. 11/120,315 filed on May 2, 2005, entitled "METHOD AND APPARATUS FOR CONVERTING OXIDIZED MERCURY INTO ELEMENTAL MERCURY;"

ii) U.S. patent application Ser. No. 11/120,317 filed on May 2, 2005, entitled "METHOD AND APPARATUS FOR DETECTING THE PRESENCE OF ELEMENTAL MERCURY IN A GAS SAMPLE;"

iii) U.S. patent application Ser. No. 11/120,316 filed on May 2, 2005, entitled "METHOD AND APPARATUS FOR GENERATING OXIDIZED MERCURY HAVING A MEASURABLE CONCENTRATION;"

iv) U.S. patent application Ser. No. 11/120,182 filed on May 2, 2005, entitled "METHOD AND APPARATUS FOR MONITORING MERCURY IN A GAS SAMPLE;"

the entire teachings of which are hereby incorporated by this reference.

FIELD OF THE INVENTION

Embodiments of the present disclosure relate to a system and method for testing integrity of a mercury monitoring system and, more particularly, to i) calibration of a elemental mercury gas detector device in the mercury monitoring system, and ii) testing the ability of a converter in the mercury monitoring system to convert oxidized mercury gas into elemental mercury gas. Additional embodiments of the present disclosure are discussed in more detail below.

BACKGROUND

Emissions from fossil fuel combustion facilities, such as flue gases of coal-fired utilities and municipal solid waste incinerators, typically include mercury. The emissions include vaporized mercury as elemental mercury, $Hg^0$, and/or as part of mercury-containing compounds (e.g., an oxidized form of mercury ($Hg^{+2}$), such as in mercuric chloride or mercuric nitrate).

Many countries regulate emissions of mercury within waste gases because of potential environmental hazards posed by the mercury emissions. Hence, facilities generating gas emissions that can contain mercury typically utilize a mercury monitoring system to measure total mercury concentration in the emissions to comply with the regulations. Certain mercury monitoring systems include a converter that converts the oxidized mercury within the emissions into elemental mercury, such as by using a mercury converter performing a thermal conversion or cracking process. The mercury monitoring systems then measure the total amount or concentration of elemental mercury within the emissions using an analyzer, such as an atomic fluorescence spectrometer.

To ensure accurate measurement of the elemental mercury concentration within the emissions, the mercury monitoring systems typically include a calibration assembly. A conventional calibration assembly provides vaporized elemental mercury to the analyzer at a particular concentration. The analyzer compares the amount of elemental mercury with that of dry, substantially mercury-free gas, such as provided by a dilution gas supply. The results of the comparison allow an operator to calibrate the mercury monitoring system.

SUMMARY

As described above, conventional calibration assemblies within mercury monitoring systems utilize vaporized elemental mercury to calibrate the mercury analyzer of the mercury monitoring system. However, certain mercury monitoring systems such as continuous emission monitoring systems require calibration for accurate response to both elemental mercury and oxidized mercury. And while commercial sources of elemental mercury are available for use in calibrating conventional mercury monitoring systems, reliable and accurate standards for oxidized mercury are typically not readily available for use in calibrating mercury monitoring systems.

Configurations of the present calibration assembly generate oxidized mercury in known concentrations for calibrating components (e.g., a mercury converter or mercury analyzer) of a mercury monitoring system. The calibrator generates elemental mercury having a known elemental mercury concentration, $[Hg^0]$, and combines an oxidizing component with the elemental mercury, thereby reducing the concentration of elemental mercury to $[Hg^0]_2$. The difference between $[Hg^0]_1$ and $[Hg^0]_2$ is substantially equal to the concentration of oxidized mercury produced by the calibrator. By providing oxidized mercury at a known concentration, the calibrator allows a user to calibrate continuous emission monitoring systems for accurate response to both elemental mercury and oxidized mercury.

In one arrangement, a mercury monitoring system calibrator includes a reactor, an elemental mercury source coupled to the reactor, an oxidizing component source coupled to the reactor, and a controller in communication with the reactor. The elemental mercury source is configured to deliver a first concentration of elemental mercury to the reactor. The oxidizing component source is configured to deliver an oxidizing component to the reactor. The reactor combines the oxidizing component with at least a portion of the elemental mercury to form an output. Based upon the difference between the first concentration of elemental mercury and the second concentration of elemental mercury within the output, the device generates a known concentration of oxidized mercury within the output. Thus the mercury monitoring system calibrator generates oxidized mercury having a known concentration. By providing oxidized mercury at a known concentration, the mercury monitoring system calibrator allows a user to calibrate continuous emission monitoring systems for accurate response to both elemental mercury and oxidized mercury.

Embodiments herein include a mercury monitoring system that switches between dual channels (e.g., different delivery flow paths) to continuously monitor elemental and oxidized mercury, with oxidized mercury determined as the difference in the elemental mercury detected in the output flows of the two channels. Humidifying the mercury calibration gas sample enhances a flow of the calibration gas sample through the channels of the mercury monitoring system.

More specifically, according to one embodiment herein, a mercury monitoring system includes a mercury calibration subsystem. The mercury monitoring system can be selectively configured to receive a gas sample produced by the mercury calibration subsystem or alternatively receive flue gas (e.g., exhaust from an industrial facility that potentially includes pollutants). To ensure accurate analysis of the flue gas, the mercury monitoring system is at least occasionally calibrated (e.g., tested) with one or more gas samples provided by the mercury calibration subsystem to ensure the integrity of the mercury monitoring system. After calibration, the mercury monitoring system can be used to test the presence of mercury pollutants (e.g., elemental mercury, oxidized mercury, etc.) in the flue gas sample.

As mentioned above, the mercury monitoring system can be configured to include multiple flow paths (e.g., dual channels) for measuring mercury. As an example, a first flow path of the mercury monitoring system includes a converter that converts oxidized mercury gas into elemental mercury gas. An output of the converter in the first flow path feeds into a detector capable of detecting an amount of elemental mercury gas in a received sample (e.g., a flue gas sample or calibration sample). When the first flow path is selected, the detector detects a presence of a total amount of mercury in a sample including i) an original amount of elemental mercury in the gas sample as well as ii) any elemental mercury derived from conversion of oxidized mercury into elemental mercury by the converter.

A second flow path of the mercury monitoring system also directs a gas sample to the detector as discussed above. However, the second flow path bypasses the converter. Accordingly, the second flow path does not convert oxidized mercury of a gas sample into elemental mercury. When the second flow path is selected, the detector only detects a presence of original elemental mercury in the gas sample and not oxidized mercury converted into elemental mercury by a converter.

A mode controller of the mercury monitoring system selectively controls switching of a selected gas sample (e.g., a flue gas sample or a calibration sample) between the first and second flow paths. Switching between receipt of a gas sample on the first and second flow path enables the mercury monitoring system to identify (e.g., measure via use of the same detector) an original amount of elemental mercury gas present in the sample as well as identify an original amount of oxidized mercury gas in a gas sample. For example, the mercury monitoring system utilizes the detector to measure an amount of original elemental mercury in the sample gas as received on the second flow path. After switching, the mercury monitoring system measures a total amount of mercury in the gas sample as received on the first flow path, since the converter in the first flow path has converted any oxidized mercury into elemental mercury. Based on continuous measurements in the first and second flow paths for a given gas sample, the mercury monitoring system can deduce how much oxidized mercury (e.g., mercury halide) is present in the gas sample. For example, a difference between the measurements of elemental mercury present in the first flow path and the second flow path indicates how much mercury compound in the sample was converted into elemental mercury gas by the converter in the first flow path.

The mercury monitoring system is at least occasionally calibrated (e.g., tested) with gas samples provided by the mercury calibration subsystem. For example, to calibrate the detector of the mercury monitoring system, the mercury calibration subsystem produces a first gas sample including a known concentration of elemental mercury gas with little or no oxidized mercury in the gas sample. The mode controller of the mercury monitoring system initiates switching between delivering the first gas sample to the detector on the first flow path and the second flow path. Readings by the detector for the first flow path and the second flow path should be substantially the same because the first gas sample includes little or no oxidized mercury converted into elemental mercury by the converter in the first flow path. Based on this initial gas sample, the detector is calibrated so that the detector properly measures an amount of elemental mercury in future gas samples.

Calibration of the detector can include hardware and/or software adjustments associated with the detector so that future readings of the detector more accurately reflect how much elemental mercury is in a gas sample. Accordingly, one embodiment herein includes producing a gas sample to have a known concentration of gaseous elemental mercury (e.g., 10 micrograms per cubic meter) and repeatedly switching between receipt of the gas sample on first and second flow paths to calibrate the detector by exposing the detector to the known concentration of gaseous elemental mercury.

In addition to calibrating and/or testing the detector, the efficiency of the converter in the first flow path can be occasionally tested to ensure its proper operation. Otherwise, the mercury monitoring system may not properly measure the total mercury present in a flue gas sample. In other words, a flue gas sample may include a high level of mercury compounds (e.g., oxidized mercury) and little or no elemental mercury gas. If the converter does not efficiently (e.g., completely) convert substantially all of the mercury compounds (e.g., oxidized mercury) in the flue gas to elemental mercury, then the detector will be unable to detect a total amount of mercury in the flue gas sample.

To test the efficiency (e.g., an ability of the converter to convert oxidized mercury in the gas sample to elemental mercury) of the converter, the mercury calibration subsystem produces a second gas sample. For example, the mercury calibration subsystem produces a second gas sample by reacting elemental mercury gas received from a elemental mercury gas source with an oxidizing component received from an oxidizer gas source. The elemental mercury gas received from the first gas source has a known concentration (e.g., 10 micrograms/cubic meter). The oxidizing component converts at least a portion of the known concentration of elemental mercury from the first gas source into oxidized mercury gas such that the second gas sample includes a mixture of an unknown concentration of elemental mercury gas and an unknown concentration of oxidized mercury gas. After producing the gas sample, the mode controller of the mercury monitoring system selectively switches between delivering the second gas sample on the first flow path and the second flow path to the detector. Prior to switching from one channel to the other, the detector measures elemental mercury in the gas sample one or more times.

The mercury calibration subsystem can include a flow controller that controls a flow of the oxidizing component received from an oxidizer gas source to limit how much of the elemental mercury provided from the elemental mercury gas source is converted into the oxidized mercury gas. For example, the flow controller can control and provide enough oxidizing component (e.g., chlorine, bromine, ozone, $NO_3$, etc.) to convert 75% of the elemental mercury (e.g., of an original concentration of 10 micrograms/cubic meter) into oxidized mercury while 25% remains as elemental mercury.

When this sample is switched between the first and second flow paths, the detector should detect a presence of 2.5 micrograms/cubic meter on the second flow path (which does not include the converter) and 10 micrograms/cubic meter on the first flow path since (ideally all of) the oxidized mercury in the gas sample will be converted into elemental mercury on the first flow path. Thus, measurements associated with the first flow path will indicate a total amount of mercury present in a sample. If the detector detects that the gas sample on the first flow path (e.g., the total mercury measurement channel which happens to include the converter) does not have an associated concentration of elemental mercury substantially equal to the known concentration of elemental mercury gas (e.g., 10 micrograms/cubic meter) initially present in the gas sample, the mercury monitoring system produces and utilizes a correction factor for adjusting future measurement readings provided by the detector when sampling on the first flow path. Thus, this integrity check involves testing an ability of the converter to convert oxidized mercury into elemental mercury.

Accordingly, embodiments herein include testing efficiency of the converter in the first flow path by: i) starting with a known concentration of elemental mercury gas initially in a calibration gas sample; ii) converting a portion of the elemental mercury in the calibration gas sample to oxidized mercury such that the gas sample includes an unknown concentration of elemental mercury and an unknown concentration of oxidized mercury; iii) delivering the calibration gas sample including the unknown concentration of elemental mercury and unknown concentration of oxidized mercury along a flow path (including the converter) to the detector, the converter converting the unknown concentration of oxidized mercury back into elemental mercury; and iv) verifying whether the detector detects that the delivered calibration gas sample has a concentration of elemental mercury substantially equal to the known concentration of elemental mercury gas initially in the gas sample.

Additional embodiments herein include verifying efficiency of the converter device in the first path over a range of different concentrations of oxidized mercury. Note that an ideal converter will convert 100% of the oxidized mercury into corresponding elemental mercury gas regardless of a concentration of oxidized mercury to be converted into elemental mercury. However, converter efficiency often varies depending on concentration of the oxidized mercury to be converted. Based on sampling of gases having different concentrations of oxidized mercury at different times, the mercury monitoring system as discussed herein can identify the appropriate correction factors to apply for different detected concentrations of elemental mercury for more accurately determining actual concentrations of oxidized mercury in a flue gas sample.

As an example, the mercury calibration subsystem can produce multiple different sample gases having different concentrations of oxidized mercury to elemental mercury. In such a configuration, the mercury calibration subsystem controls a flow rate of oxidizing component from a oxidizing agent source so that, for example, 25% oxidized mercury gas and 75% elemental mercury are produced. For this first time duration, the mercury monitoring system switches between delivering the gas sample to the detector on the first and second flow paths to identify an amount of elemental mercury and oxidized mercury present in the gas sample as previously discussed. Based on measurements by the detector on the first and second flow paths, the mercury monitoring system identifies whether converter efficiency is below 100% for the given concentration of oxidized mercury (e.g., 25% oxidized mercury or 2.5 micrograms/cubic meter) in the gas sample. If necessary, the mercury monitoring system produces a correction factor associated with the converter for the given concentration level of oxidized mercury so that future measurements of elemental mercury received on the first flow path are more accurate for a particular concentration.

After testing the above gas sample, the mercury calibration subsystem can control a flow rate of oxidizing component so that a different amount of oxidized mercury gas is produced (e.g., 75% oxidized mercury, with 25% elemental mercury remaining). For a second time duration, the mercury monitoring system switches between delivering this gas sample to the detector on the first and second flow paths to identify an amount of elemental mercury and oxidized mercury present in the gas sample as previously discussed. Based on measurements by the detector on the first and second flow paths, the mercury monitoring system identifies whether converter efficiency is below 100% for the given concentration of oxidized mercury in the gas sample. If necessary, the mercury monitoring system produces a correction factor associated with the converter for the given concentration of oxidized mercury.

Any number of different concentrations of oxidized mercury gas can be produced and used to verify the efficiency of the converter.

The mercury calibration subsystem as discussed herein can include a humidity controller device in order to modify (e.g., increase or decrease) the relative humidity of a gas sample so that the relative humidity of a mercury gas sample is in a specified range. Humidifying (e.g., elemental mercury and/or oxidized mercury) enhances a flow of the gas sample along the first flow path and the second flow path as discussed above. In other words, adjusting the relative humidity of the gas sample can ensure that the elemental mercury and/or oxidized mercury in a gas sample does not stick to the walls of a conduit, filter etc. in the flow paths from a gas source to the detector.

Modifying a relative humidity associated with a gas sample used for calibration can be done to simulate a relative humidity of a flue gas sample that is tested for presence of mercury after calibration. Accordingly, measurements associated with the flue gas sample can be more accurate because the mercury monitoring system is calibrated under similar environmental conditions as the flue gas sample under test.

In a specific configuration, the mercury calibration subsystem receives elemental mercury gas from an elemental mercury gas source. The mercury calibration subsystem modifies a relative humidity level of the elemental mercury gas by passing the elemental mercury gas through a humidifier device. The mercury calibration subsystem also receives an oxidizing component from an oxidizing component source and mixes/reacts the elemental mercury gas (as received from the elemental mercury gas source through the humidifier) with the oxidizing component in a mixing chamber to produce a gas sample. The gas sample produced by the mixing chamber is used to calibrate and/or test the mercury monitoring system as discussed above.

Accordingly, embodiments herein include repeatedly switching between delivery of gas (calibration) samples on a first path (including a converter) and second flow path (not including a converter) to verify at least one of: i) an ability of the detector to properly detect a presence of elemental mercury gas in a sample, and ii) an ability of the converter to convert elemental mercury gas into oxidized mercury gas. Passing the integrity checks according to embodiments herein provides an assurance that the mercury monitoring system can properly detect a presence of mercury in a flue gas sample. As discussed above, inclusion of a humidity controller enhances a flow of a gas sample through the mercury monitoring system.

BRIEF DESCRIPTION OF THE DRAWINGS

The foregoing and other objects, features and advantages of the methods and apparatus will be apparent from the following description of particular embodiments, as illustrated in the accompanying drawings in which like reference characters refer to the same parts throughout the different views. The drawings are not necessarily to scale, emphasis instead being placed upon illustrating the principles of the apparatus.

DETAILED DESCRIPTION

Configurations of the present calibration assembly generate oxidized mercury in known concentrations for calibrating components (e.g., a mercury converter or mercury analyzer) of a mercury monitoring system. The calibrator generates elemental mercury having a known concentration, $[Hg^0]$, and combines with it an oxidizing component, thereby reducing the concentration of elemental mercury to $[Hg^0]_2$. The difference between $[Hg^0]_1$ and $[Hg^0]_2$ is substantially equal to the concentration of oxidized mercury produced by the calibrator. By providing oxidized mercury at a known concentration, the calibrator allows a user to calibrate continuous emission monitoring systems for accurate response to both elemental mercury and oxidized mercury.

Figure 1:
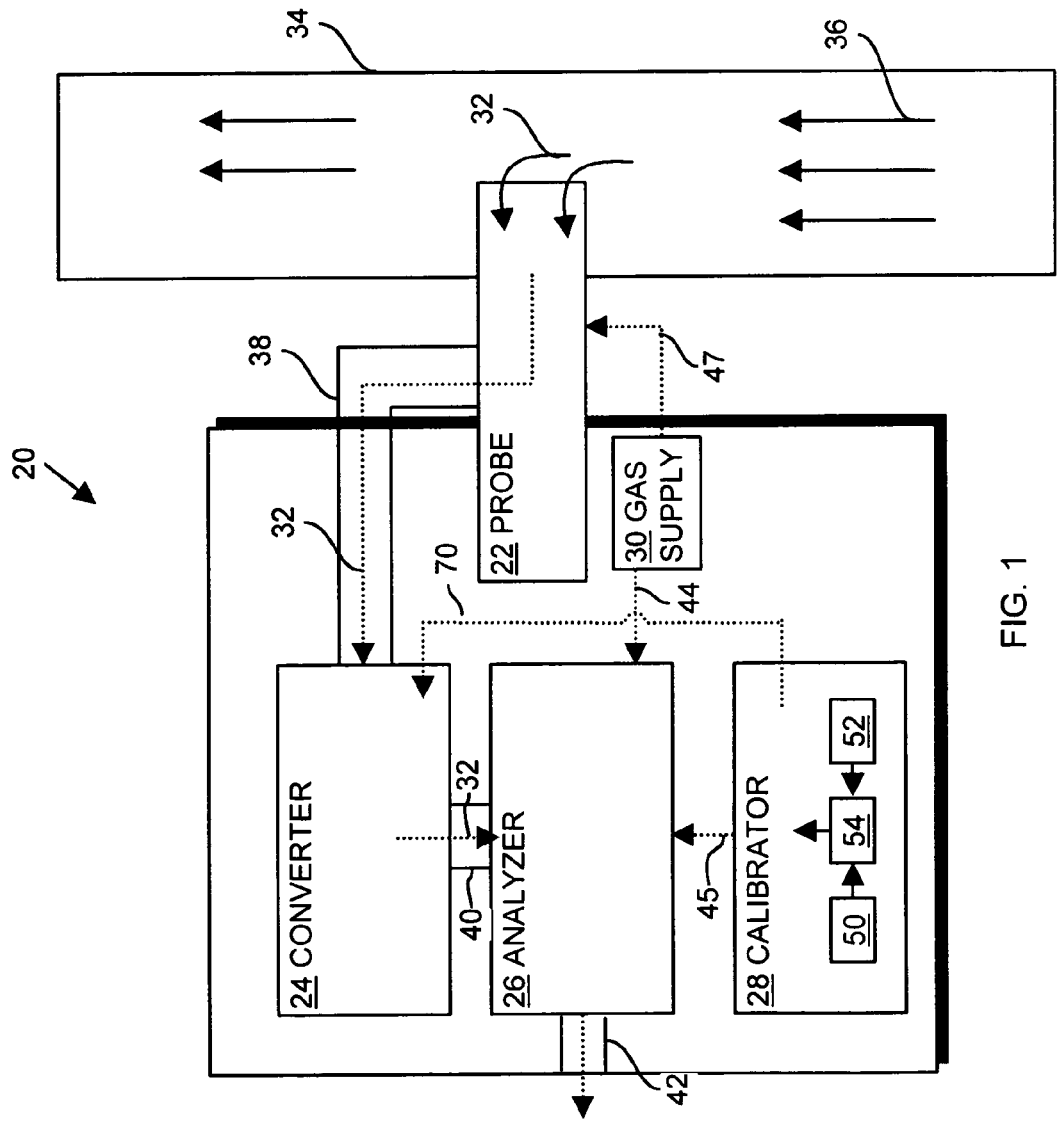
FIG. 1 is a schematic of a mercury monitoring system.

FIG. 1 illustrates a mercury monitoring system 20 for monitoring total mercury within a fluid sample, such as in an effluent gas from a coal-fired power plant, in a substantially continuous manner. The mercury monitoring system 20, or Continuous Emission Monitoring System (CEMS), includes a probe 22, a converter 24, an analyzer 26, a calibrator 28, and a dilution gas supply 30.

The probe (e.g., extraction probe) 22 is configured to receive a gas sample 32 from a sample source and deliver the gas sample 32 to the converter 24. For example, the probe 22 extends into, or is mounted proximate to, a stack or flue 34 of a coal combustion facility and collects, as the gas sample 32, a portion of the fluid or gas (e.g., effluent or emission) 36 flowing through the stack 34. The probe 22, in one arrangement, includes an inertial filter that separates particulate matter (e.g., flue ash) from the gas sample 32. Surfaces of the probe 22 that contact the gas sample 32 typically have a coating (e.g., glass) that minimizes or prevents chemical reactions between the probe 22 and mercury present within the gas sample 32.

The probe 22 is connected to the converter 24 by way of a heated conduit 38 maintained at a temperature of, for example, 150° C. The heated conduit 38 limits condensation of the gas sample 32 and "sticking" of vaporized mercury to the conduit 38 and provides efficient transport of the gas sample 32 to the converter.

The converter 24 receives the gas sample 32 from the probe 22 and is operable to convert the vapor-phase species of mercury (e.g., oxidized mercury) present within the gas sample 32 into elemental mercury and to maintain the mercury in the elemental form so as to allow the analyzer 26 to detect the total mount of mercury present within a gas sample. For example, in one arrangement, the converter 24 converts oxidized forms of mercury, $Hg^{+2}$ (e.g., $HgCl_2$, $Hg(NO_3)_2$) into elemental mercury, $Hg^0$, by applying a relatively high temperature to the gas sample 32.

The analyzer 26 is connected to the converter 24 by way of a heated conduit 40 and receives the heated gas sample 32 from the converter 24. In one arrangement, the analyzer 26 is an atomic fluorescence analyzer that measures or detects an amount or a concentration of elemental mercury present within the gas sample 32. Upon completion of the detection process, the analyzer 26 exhausts the gas sample 32 to the atmosphere via an exhaust port 42.

Typically, the analyzer 26 requires periodic calibration in order to accurately detect or measure the presence of elemental mercury within a gas sample 32. Calibration is provided by the calibrator 28 which, in one arrangement is in fluid communication with the analyzer 26 through a line or conduit 45 and provides vaporized elemental mercury to the analyzer 26 at a particular concentration, such as by using a Peltier cooler/vapor pressure control and mass flow controllers. The analyzer 26 compares the amount of elemental mercury received from the calibrator 28 with that of dry, substantially mercury-free gas, received from the dilution gas supply 30 via conduit 44. The results of such a comparison allow direct calibration of the analyzer 26.

In certain cases, the analyzer 26 requires periodic calibration in order to accurately detect or measure the presence of both elemental and oxidized mercury within a gas sample 32. The calibrator 28 is connected to the converter 24 and provides a known concentration of oxidized mercury, such as in the form of a mercury-containing vapor, to the converter 24. By providing oxidized mercury having a known concentration, the calibrator 28 allows calibration of the analyzer 26 within the mercury monitoring system 20.

Figure 2:
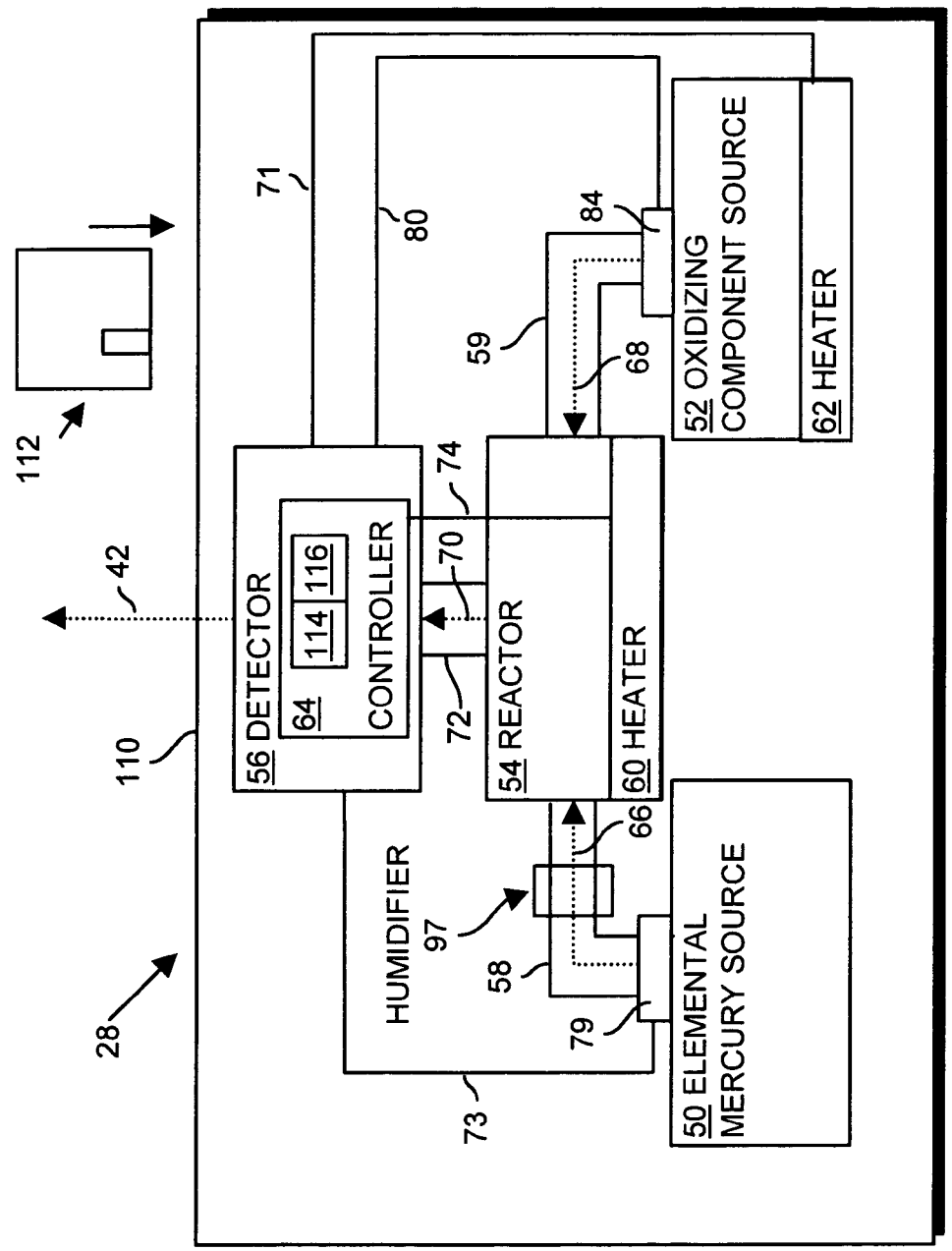
FIG. 2 illustrates an arrangement of a mercury system calibrator as used within the mercury monitoring system of FIG. 1.

FIG. 2 illustrates an arrangement of the calibrator 28. The calibrator 28 includes an elemental mercury source 50, an oxidizing component source 52, and a reactor 54 coupled to the elemental mercury source 50 and the oxidizing component source 52.

The elemental mercury source 50 is connected to the reactor by a conduit 58 and provides a stream of elemental mercury 66, having a known concentration, to the reactor 54. For example, in one arrangement, the elemental mercury source 50 includes a vapor generator with liquid elemental mercury that evaporates into elemental mercury in response to application of a particular pressure and temperature. In such an arrangement, the vapor generator (e.g., elemental mercury source 50) enables a flow of gas or air (e.g., substantially mercury-free gas) through the evaporated elemental mercury and delivers the vaporized mercury to the reactor 54 as a vapor stream having a known (e.g., operator determined) concentration of vaporized mercury within the vapor stream.

In another arrangement, the elemental mercury source 50 includes a permeation device. The permeation device contains elemental mercury in a two-phase state (liquid and gas). At a substantially constant temperature, the permeation device emits gaseous elemental mercury at a substantially constant rate through a permeable element (e.g., Teflon housing) and the elemental mercury gas 66 is delivered to the reactor 54 via the conduit 58.

The calibrator 28 can include a humidifier device 97 through which the elemental mercury gas 66 passes prior to being delivered to reactor 54. In one embodiment, the humidifier device 97 includes a Model MH-110-48F-4 Nafion dryer manufactured by Perma Pure, LLC, Toms River, N.J. Such a device can include a vessel filled with distilled water that produces water vapor that is added to the mercury gas 66 passing through conduit 58. Thus, humidifier device 97 can add (or potentially remove) water vapor to change (e.g., increase or decrease) a relative humidity level of the elemental mercury gas 66 in conduit 58. In one configuration, the humidifier device 97 generates a relative humidity level of the elemental mercury gas 66 of greater than 20%, such as in a range between 50% and 80%. The temperature in or around a vicinity of the humidifier device 97 and corresponding conduit 58 may be in the range of about 15 to 45 degrees Celsius. However, note that an amount of water vapor added to the mercury gas 66 passing through conduit 58 can be adjusted within different relative humidity ranges for different temperatures so that the elemental mercury gas 66 does not condense downstream.

One purpose of humidifying (e.g., increasing an amount of water vapor in the) elemental mercury gas 66 via humidifier device 97 is to reduce a "stickiness" associated with the gaseous mercury (e.g., elemental mercury gas 66, mercury halide in output 70, etc.). For example, increasing a concentration of water vapor reduces the likelihood that gaseous mercury 66 will stick to the walls of conduit 58, reactor 54, conduit 72, etc. as the gaseous mercury progresses towards detector 56. Reducing an amount of mercury deposited on the walls of conduit 58, reactor 54, etc. ensures that such deposits do not (or minimally) interfere with future reactions of producing output stream 70.

The oxidizing component source 52 is connected to the reactor 54 by a conduit 59 and provides a mercury oxidizing component 68 to the reactor 54. For example, the oxidizing component source 52 provides chlorine (e.g., $Cl_2$) to the reactor 54 to oxidize the elemental mercury 66 received by the reactor 54. In one arrangement, the oxidizing component source 52 is configured as a container holding a chlorine generating chemical that, upon heating, generates chlorine in a gaseous phase.

In one arrangement, the oxidizing component source 52 includes a heater 62 and a mercury oxidizing component 68 such as palladium chloride (e.g., $PdCl_2$) or tungsten chloride in solid form. In such cases, the heater 62 increases the temperature of the palladium chloride within the oxidizing component source 52 to cause thermal separation of the palladium component from the chlorine component. The separated chlorine is then directed from the oxidizing component source 52 to the reactor 54 as chlorine gas 68. In another arrangement, the oxidizing component may be delivered from a gas cylinder.

In yet an another arrangement, the oxidizing component source can be a nitrate source such as lead nitrate. Thermal separation of nitrate occurs when exposing the lead nitrate to a sufficient temperature.

The reactor 54 is configured to receive elemental mercury 66 from the elemental mercury source 50 and the mercury oxidizing component (e.g., chlorine) 68 from the oxidizing component source 52 and combine the oxidizing component 68 with the elemental mercury 66 to form an output or output stream 70 that includes elemental mercury gas (assuming that not all of the mercury from elemental mercury source 50 is oxidized) and mercury chloride ($HgCl_2$) gas. The reactor 54, in one arrangement, defines a chamber for mixing of the elemental mercury gas 66 and the chlorine gas 68 and includes a heater 60, such as a heating coil in thermal communication with the chamber. The heater 60 delivers thermal energy (e.g., heat) to the chamber to promote combining of the elemental mercury gas 66 and the chlorine gas 68 to form mercury chloride ($HgCl_2$).

As indicated above, the calibrator 28 generates known concentrations of oxidized mercury for calibrating continuous emission monitoring systems requiring accurate responses to both elemental mercury and oxidized mercury. The following describes an example of operation of the calibrator 28.

Figure 3:
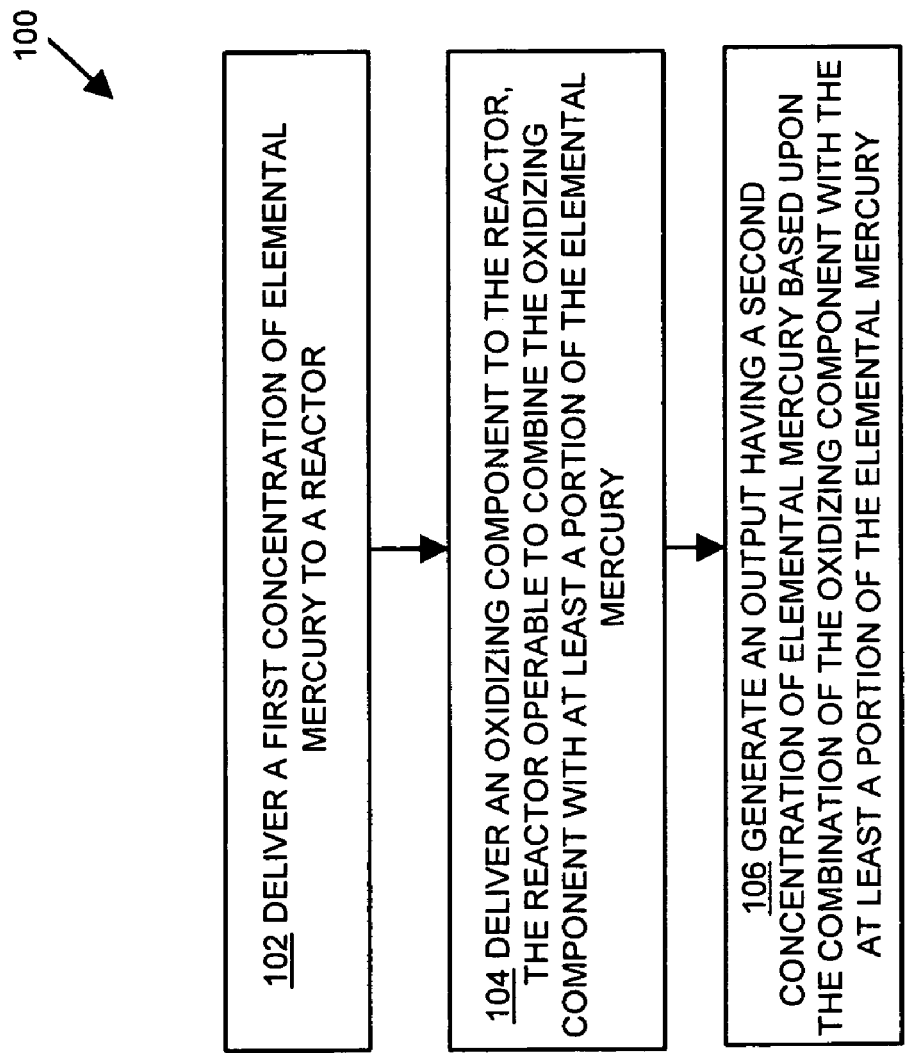
FIG. 3 is a flow chart of a procedure performed by the mercury system calibrator of FIG. 2
Figure 4:
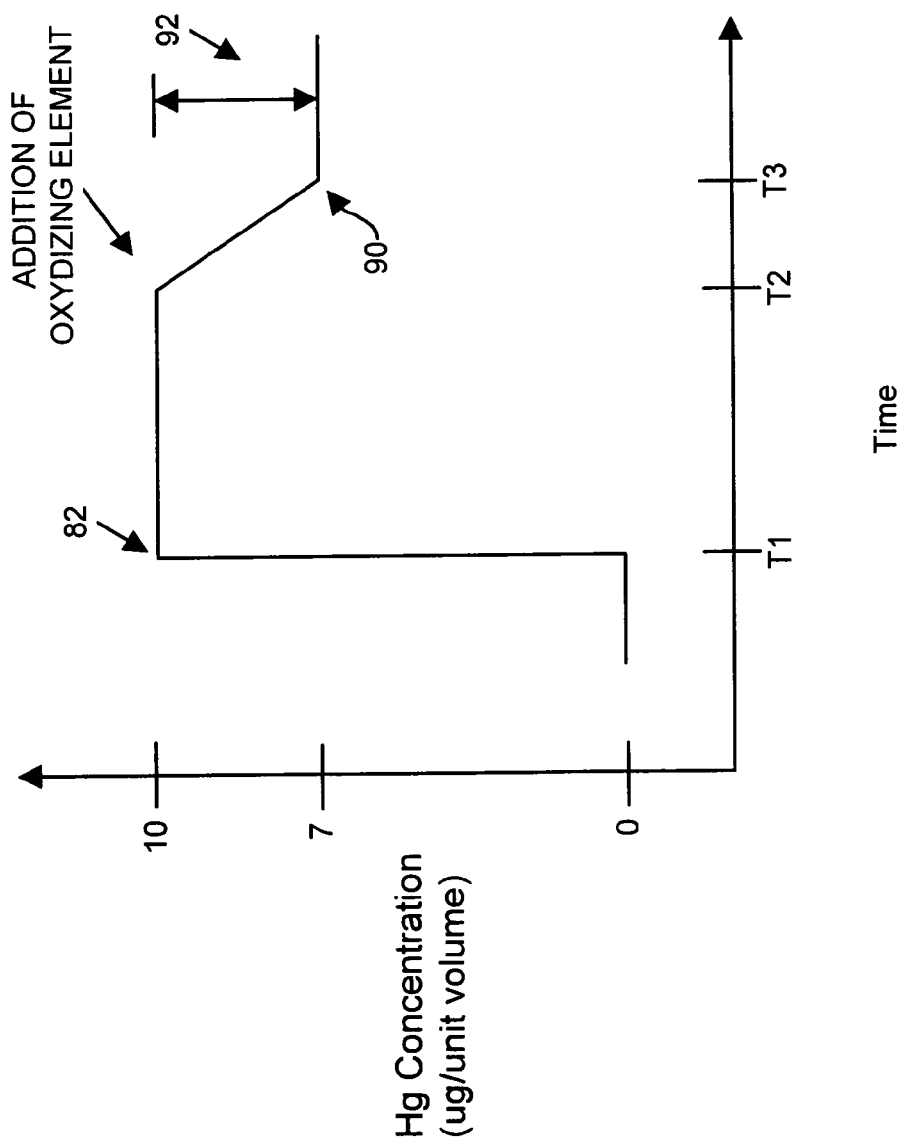
FIG. 4 is a graph illustrating detection of oxidized mercury generated by the mercury system calibrator.

FIG. 3 is a flow chart 100 of a procedure performed by the calibrator 28 to generate a known concentration of oxidized mercury for calibration of a mercury monitoring system 20. FIG. 4, taken in conjunction with FIG. 3, illustrates a concentration of elemental mercury within the output 70 during the procedure (e.g., before and after addition of the mercury oxidizing component 68 to the elemental mercury gas 66 held by the reactor 54).

In step 102, in the calibrator 28, the elemental mercury source 50 delivers a first concentration of elemental mercury 66 to a reactor 54. For example, the elemental mercury source 50 of the calibrator 28 generates an elemental mercury stream 66 having a known or first elemental mercury concentration value, $[Hg^0]_1$. As illustrated in FIG. 4, at a first time T1, the elemental mercury stream 66 (which is flowing from the elemental mercury source 50 via the conduit 58 to the reactor 54) may have a first, known concentration value 82 of 10 micrograms/unit volume.

Returning to FIG. 3, in step 104, the oxidizing component source 52 in the calibrator 28 delivers an oxidizing component 68 to the reactor 54, which may be operated at approximately room temperature (e.g., 22° C.) or an elevated temperature such as between 200 and 500 degrees Celsius. The reactor 54 combines the oxidizing component 68 with the elemental mercury 66. For example, as illustrated in FIG. 4, at a second time T2, the oxidizing component source 52 provides chlorine gas (e.g., $Cl_2$) 68 to the reactor 54 as a fluid flow, carried by the conduit 59, to oxidize the elemental mercury 66 received by the reactor 54. As indicated above, the reactor 54 defines a chamber that allows for mixing of the elemental mercury (e.g., gas) 66 and the chlorine gas 68 to form mercury chloride ($HgCl_2$) gas. In one arrangement, the reactor receives a thermal input (e.g., heat) from the heater 60 to promote rapid combining of the chlorine gas 68 with the elemental mercury 66 to form mercury chloride ($HgCl_2$) gas.

Returning to FIG. 3, in step 106 the calibrator 28 generates an output 70 having a second concentration of elemental mercury (e.g., at least a portion of the elemental mercury) based upon the combination of the oxidizing component 68 with the elemental mercury 66. Since the chlorine gas 68 combines with a portion (e.g., a percentage) of the elemental mercury 66 present within the reactor to form mercury oxide gas, as illustrated in FIG. 4 in the interval between the second time T2 and a third time T3, the concentration of elemental mercury within the reactor 54 decreases from the concentration delivered to the reactor 54 from the elemental mercury source 50. For example, the concentration of elemental mercury decreases from a first concentration 82 of 10 micrograms/unit volume to a second concentration 90 of 7 micrograms/unit volume. The calibrator 28 releases the output 70 (e.g., output stream) having the second concentration 90.

Returning to FIG. 2, in one arrangement, the calibrator 28 includes a detector 56. The detector 56 is connected to the reactor 54 via a conduit 72 and is configured to receive the output stream 70 from the reactor 54. The detector 56 includes a controller 64, such as a processor 114 and a memory 116. The detector 56, such as an atomic fluorescence spectrometer, in conjunction with the controller 64, is configured to detect a concentration of elemental mercury within the output 70. For example, the detector 56 utilizes atomic fluorescence spectroscopy to measure the concentration of elemental mercury present within the reactor output 70. The detector 56 (e.g., the controller 64 of the detector 56) also compares the concentration of elemental mercury 66, $[Hg^0]_2$ (e.g., the second concentration 90 of elemental mercury) present within the reactor output 70 with the known concentration of elemental mercury 66 produced by the elemental mercury source 50. The detected difference in elemental concentrations allows for the calculation of a concentration of oxidized mercury within the output 70, as described below.

For example, the detector 56 calculates a difference between the first concentration 82 of elemental mercury and the second concentration 90 of elemental mercury within the output 70 to detect a concentration of oxidized mercury within the output 70. For example, the controller 64 receives a second concentration value of the elemental mercury within the output 70 from the detector 56. The controller 64 subtracts the second, reduced elemental mercury concentration $[Hg^0]_2$ from the first, known elemental mercury concentration $[Hg^0]_1$. The difference between $[Hg^0]_1$ and $[Hg^0]_2$, illustrated in FIG. 4 as a change 92 in the elemental mercury concentration, is substantially equal to the concentration of oxidized mercury (e.g., $HgCl_2$) produced by the calibrator 28. By providing oxidized mercury at a measurable concentration, the calibrator 28 allows a user to calibrate continuous emission monitoring systems 20 for accurate response to both elemental mercury and oxidized mercury.

Returning to FIG. 2, in one arrangement, the controller 64 controls the thermal output of the heater 60 of the reactor 54 through an electrical line 74. The controller 64 activates the heater 60 associated with the reactor 54 to provide heat to the elemental mercury 66 and oxidizing component 68 within the reactor 54, promoting the formation of oxidized mercury. The controller 64 may also adjust the thermal output of (e.g., level of heat provided by) the heater 60 to adjust the rate of combination of the elemental mercury 66 and oxidizing component 68 and thus the concentration of oxidized mercury present within the output 70.

During operation, the controller 64 calculates the concentration of oxidized mercury within the output 70. In the case, for example, where a particular application requires the calibrator 28 to produce oxidized mercury at a particular preset concentration, the controller 64 compares a preset oxidized mercury concentration value (e.g., threshold value) with a calculated oxidized mercury value. If the preset oxidized mercury concentration value is not equal to the calculated oxidized mercury value, the controller 64 adjusts the thermal output of the heater 60 to either raise or lower the temperature of the reactor 54 (e.g., raise or lower the temperature of the elemental mercury 66 and the oxidizing component 68 within the reactor 54) so as to vary the extent of reaction of elemental mercury 66 and the oxidizing component 68, thereby adjusting the concentration of mercury oxide present within the output 70.

In one arrangement, the controller 64 is electrically connected to, and controls, the heater 62 associated with the oxidizing component source 52 through an electrical line 71. As indicated above, in one arrangement, the oxidizing component 68 contained by the oxidizing component source 52 is an oxidized metal, such as palladium chloride (i.e., $PdCl_2$) or tungsten chloride. During operation, the controller 64 activates the heater 62 to provide heat (e.g., the heater operates at a temperature of approximately 300° C.) to the oxidized metal, liberating chlorine gas, which flows from the oxidizing component source 52 to the reactor 54.

The controller 64, in one arrangement, is also configured to adjust a thermal output of (e.g., a level of heat provided by) the heater 62 to adjust the rate of separation of the oxidized metal into a metal component and an oxidizing component 68. By adjusting the rate of separation, the controller 64 can adjust the amount of the oxidizing component 68 delivered by the oxidizing component source 52 to the reactor 54 and thereby adjust the concentration of oxidized mercury present within the output 70.

During operation, the controller 64 calculates the concentration of oxidized mercury within the output 70. In the case, for example, where a particular application requires the calibrator 28 to produce oxidized mercury at a particular preset concentration, the controller 64 compares a preset oxidized mercury concentration value (e.g., threshold value) with a calculated oxidized mercury value. If the preset oxidized mercury concentration value is not equal to the calculated oxidized mercury value, the controller 64 adjusts the thermal output of the heater 62 to either increase or decrease the rate of separation of the oxidized metal into a metal component and an oxidizing component 68. By changing the rate of separation of the oxidized metal, the controller 64 increases or decreases the amount of the oxidizing component 68 (e.g., chlorine gas) available within the reactor 54 to chemically combine with the elemental mercury 66 within the reactor 54. As a result, the controller 64 adjusts the concentration of mercury oxide created within the reactor 54 and provided within the output 70 from the reactor 54.

In one arrangement, the controller 64 adjusts the amount of the elemental mercury 66 provided to the reactor 54 by the elemental mercury source 50 during operation. For example, in one arrangement, the controller 64 is electrically connected through an electrical line 73 to a valve 79 associated with the elemental mercury source 50 and in flow communication with the conduit 58. By increasing or decreasing the flow volume of elemental mercury 66 to the reactor 54, the controller 64 adjusts the amount of elemental mercury 66 within the reactor 54 available to chemically combine with the oxidizing component present. As a result, by adjusting the amount of the elemental mercury 66 provided to the reactor 54, the controller 64 adjusts the concentration of mercury oxide created within the reactor 54 and provided within the output 70 from the reactor 54.

For example, during operation, the controller 64 calculates the concentration of oxidized mercury within the output 70. The controller 64 compares a preset oxidized mercury concentration value (e.g., a threshold value) with the calculated oxidized mercury value. If the preset oxidized mercury concentration value is not equal to the calculated oxidized mercury value, the controller 64 adjusts (e.g., increases or decreases) the amount of the elemental mercury 66 delivered to the reactor 54, such as by adjusting the valve of the elemental mercury source 50. By adjusting the amount of the elemental mercury 66 provided to the reactor 54, the controller 64 adjusts the concentration of mercury oxide created within the reactor 54 and provided within the output 70 from the reactor 54.

In one arrangement, the controller 64 adjusts the amount of the oxidizing component 68 provided to the reactor 54 by the oxidizing component source 52 during operation. For example, in one arrangement, the controller 64 is electrically connected through an electrical line 80 to a valve 84 associated with the oxidizing component source 52 and in flow communication with the conduit 59. By increasing or decreasing the flow volume of the oxidizing component 68 to the reactor 54, the controller 64 adjusts the amount of the oxidizing component 68 within the reactor 54 available to chemically combine with the elemental mercury 66 present. As a result, by adjusting the amount of the oxidizing component 68 provided to the reactor 54, the controller 64 adjusts the concentration of mercury oxide created within the reactor 54 and provided within the output 70 from the reactor 54.

For example, during operation, the controller 64 calculates the concentration of oxidized mercury within the output 70. The controller 64 compares a preset oxidized mercury concentration value (e.g., a threshold value) with the calculated oxidized mercury value. If the preset oxidized mercury concentration value is not equal to the calculated oxidized mercury value, the controller 64 adjusts (e.g., increases or decreases) the amount of the oxidizing component 68 delivered to the reactor 54, such as by adjusting the valve of the elemental mercury source 50. By adjusting the amount of the oxidizing component 68 provided to the reactor 54, the controller 64 adjusts the concentration of mercury oxide created within the reactor 54 and provided within the output 70 from the reactor 54.

Figure 5:
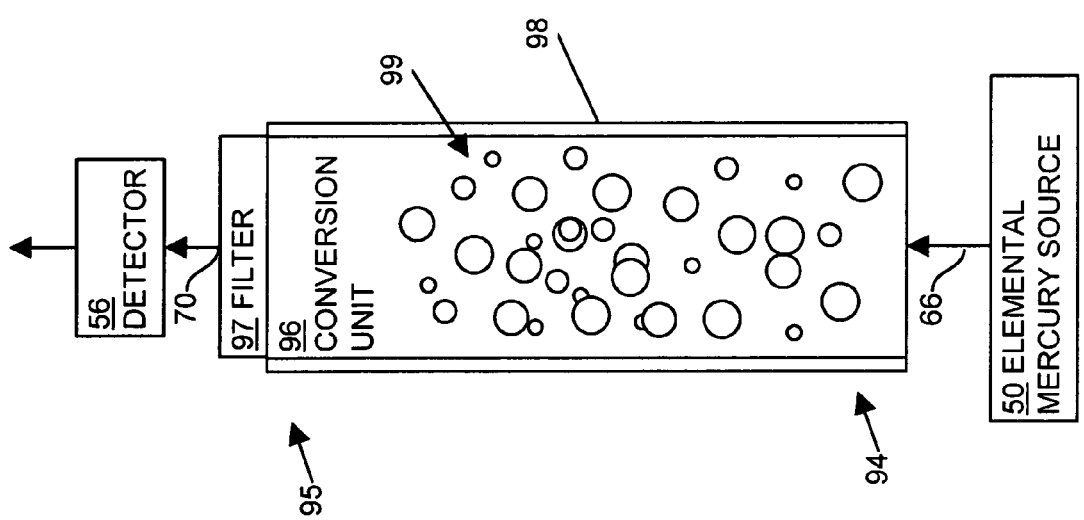
FIG. 5 illustrates an arrangement of a mercury system calibrator as used within the mercury monitoring system of FIG. 1.

FIG. 5 illustrates an arrangement of the calibrator 28 where the reactor 54 and the oxidizing component source 52 form a single, integrated conversion unit 96. Such an arrangement minimizes the number of components required by the calibrator 28 to generate a known concentration of mercury oxide.

The conversion unit 96 has a first end 94 and a second end 95. The first end 94 is connected to the elemental mercury source 50 and is operable to direct elemental mercury 66 through the conversion unit 96 toward the second end 95. The second end 95 is connected to the detector 56 and is operable to direct an output 70 (e.g., a combination of elemental mercury and oxidized mercury in gaseous phase) toward the detector 56. The conversion unit 96 includes a filter 97 and a heater 98 and contains an oxidized metal 99, such as palladium chloride (i.e., $PdCl_2$).

The heater 98 is operable to heat materials within the conversion unit 96 and serves a dual purpose. First, the heater 98 is configured to increase the temperature of oxidized metal 99 within the conversion unit 96 to cause thermal separation of the metal component from the oxidizing component. Second, the heater 98 is configured to deliver thermal energy or heat to the conversion unit 96 to increase the temperature of the elemental mercury gas 66 and the oxidizing component (e.g., chlorine gas) 68 present within the conversion unit 96. Such an increase in temperature promotes combination of the elemental mercury gas 66 and the chlorine gas 68 to form mercury chloride ($HgCl_2$).

Returning to FIG. 2, the calibrator 28, in one arrangement, is configured as a computerized device 110. A computer program product 112 includes an application or logic instructions that are loaded into the computerized device 110 to configure the device 110 to perform as a calibrator 28.

The computerized device 110 includes the controller 64 that, in one arrangement, includes a memory 114 and a processor 116. The memory 114 can be of any type of volatile or non-volatile memory or storage system such as a computer memory (e.g., random access memory (RAM), read only memory (ROM), or another type of memory) disk memory, such as hard disk, floppy disk, optical disk, for example. The memory 114 is encoded with logic instructions and/or data that, in one embodiment of the computerized device 110, form a calibrator application configured according to embodiments of the calibrator 28. In other words, the calibrator application represents software coding instructions and/or data that reside within the memory or storage 114, or within any computer readable medium accessible to the computer device 110.

The processor 116 may be any type of circuitry or processing device such as a central processing unit, controller, application specific integrated circuit, programmable gate array, or other circuitry that can access the calibrator application encoded within the memory 114 in order to run, execute, interpret, operate, or otherwise perform the calibrator application logic instructions. In other words, in another embodiment of the computer device 110, a calibrator process represents one or more portions of the logic instructions of the calibrator application while being executed or otherwise performed on, by, or in the processor 116 within the computerized device 110.

While this invention has been particularly shown and described with reference to preferred embodiments thereof, it will be understood by those skilled in the art that various changes in form and details may be made therein without departing from the spirit and scope of the invention as defined by the appended claims.

In one example, as illustrated and described with respect to FIG. 2, the detector 56 forms part of the calibrator 28. Such illustration and description is by way of example only. In an alternate arrangement, the calibrator 28 utilizes an external detector (e.g., a detector external to) the calibrator. For example, the calibrator 28 may utilize the analyzer 26 of the system 20 to perform the functions of the detector 56 described above.

FIG. 2 illustrates the detector 56 as having a single controller 64 configured to operate components of the calibrator (e.g., the elemental mercury source 50, the reactor heater 60, the oxidizing component source 52, and the oxidizing component source heater 62). Such illustration is by way of example only; in another arrangement the calibrator 28 includes separate controllers each performing one or more functions of the single controller 64 described above.

As indicated above, during operation, elemental mercury 66 flows from the elemental mercury source 50 to the reactor 54 via the conduit 58. Also during operation, the oxidizing component 68, such as chlorine gas, flows from the oxidizing component source 52 to the reactor 54 via the conduit 59. In another arrangement, the conduit 58 flows elemental mercury 66 past the oxidizing component source 52 to the reactor 54. The oxidizing component source 52 delivers the oxidizing component 68 to the reactor 54 by way of passive diffusion. Passive diffusion of the oxidizing component 68 limits or eliminates the need for a pump to force or draw the oxidizing component 68 from the oxidizing component source 52 and into the reactor 54.

FIG. 2 illustrates an arrangement of the calibrator 28 as including the elemental mercury source 50, the oxidizing component source 52, and the reactor as a single "unit". In one arrangement, the elemental mercury source 50 and the oxidizing component source 52 are located at two separate locations. For example, the elemental mercury source 50 can be located within an instrument rack while the oxidizing component source 52 is located in or within proximity to the probe 22.

Figure 6:
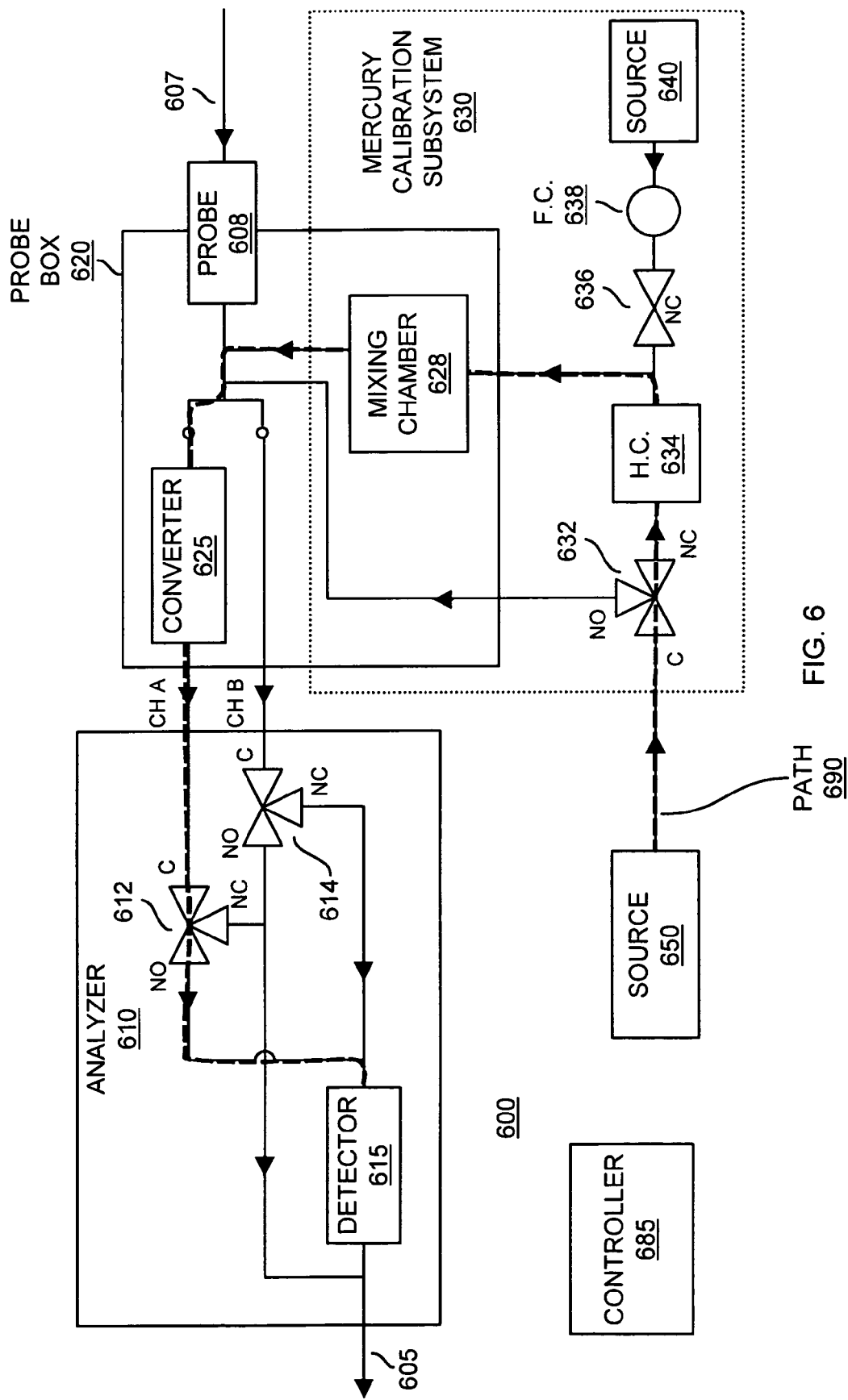
FIGS. 6-11, and 15-16 are schematics of a mercury monitoring system according to embodiments herein, and illustrating different flow paths employed for calibration/integrity checks in response to elemental and oxidized mercury and for monitoring mercury in flue gases.

FIG. 6 is a diagram illustrating a mercury monitoring system 600 with a calibrator according to embodiments herein.

As shown, mercury monitoring system 600 includes an analyzer 610, a probe box 620, mercury calibration subsystem 630, controller 685, and mercury source 650. Probe box 620 includes probe 608, converter 625, and mixing chamber 628 (e.g., a reactor). Analyzer 610 includes detector 615, valve 612, and valve 614. Mercury calibration subsystem 630 includes mixing chamber 628, valve 632, humidity controller 634, valve 636, flow controller 638, and oxidizer source 640.

Mercury monitoring system 600 includes flow conduits (e.g., pipes, tubes, etc.) connecting one element to another. Such conduits permit a gas sample from mercury source 650 (e.g., a first element) to pass to valve 632, from valve 632 to humidity controller 634, and so on. A vacuum pump (not shown) is included downstream of the analyzer 610 to draw gas samples through the monitoring system 600 and leave as exhaust 605. According to one configuration, the vacuum pump simultaneously draws a gas sample (e.g., from flue gas sample 607 or mercury calibration subsystem 630) through both channels A and B. However, the valves 612 and 614 are set such that only one of the channels is directed to detector 615 at a time. Accordingly, the detector 615 can be used to measure elemental mercury present in a gas sample on either channel A or channel B.

The mercury monitoring system 600 can be selectively configured by controller 685 to receive a gas sample produced by the mercury calibration subsystem 630 or receive flue gas 607 (e.g., exhaust from an industrial facility that potentially includes pollutants) via probe 608, one end of which protrudes into a smoke stack to receive the flue gas sample 607, the other end of which is encased in probe box 620 to selectively direct the flue gas sample 607 along channels A and B. Probe 608 can include an inertial filter, conditioners, temperature sensors, etc.

To ensure accurate analysis of flue gas 607, the mercury monitoring system 600 is initially calibrated and tested as discussed in FIGS. 6-11. The mercury monitoring system 600 can be occasionally or periodically calibrated (e.g., tested once a day, week, etc.) with one or more gas samples provided by the mercury calibration subsystem 630 to ensure the integrity of the mercury monitoring system 600. After calibration, the mercury monitoring system 600 can be used to monitor elemental mercury and oxidized mercury in flue gas sample 607, as discussed in FIGS. 14 and 15.

Referring again to FIG. 6, controller 685 of the mercury monitoring system 600 selectively controls a switching of a selected gas sample (e.g., a flue gas sample 607 from a probe 608 which extracts the sample from a stack, or flue, or a calibration sample from mercury calibration subsystem 630) between first and second flow paths (such as channel A and channel B) to detector 615. The different possible flow paths of mercury monitoring system 600 are defined by setting valve 612, valve 614, valve 632, and valve 636. Valves can be manually or automatically controlled. According to one configuration, controller 685 sets up different gas flow paths by sending electrical signals along electrical lines (not shown) to open and close the above mentioned valves in mercury monitoring system 600.

Port C of valves 612, 614, 632 serve as a collector or input. The output of valve 612, valve 614, and valve 632 can be configured to enable a flow from input port C to the output of port NC or port NO based on control signals from controller 685. Valve 636 can be turned on and off (by controller 685) to enable a flow of gas (e.g., an oxidizing component such as chlorine gas) to mixing chamber 628. Accordingly, the controller 685 can effectively direct a gas sample along any of multiple appropriate flow paths to detector 615.

Figure 7:
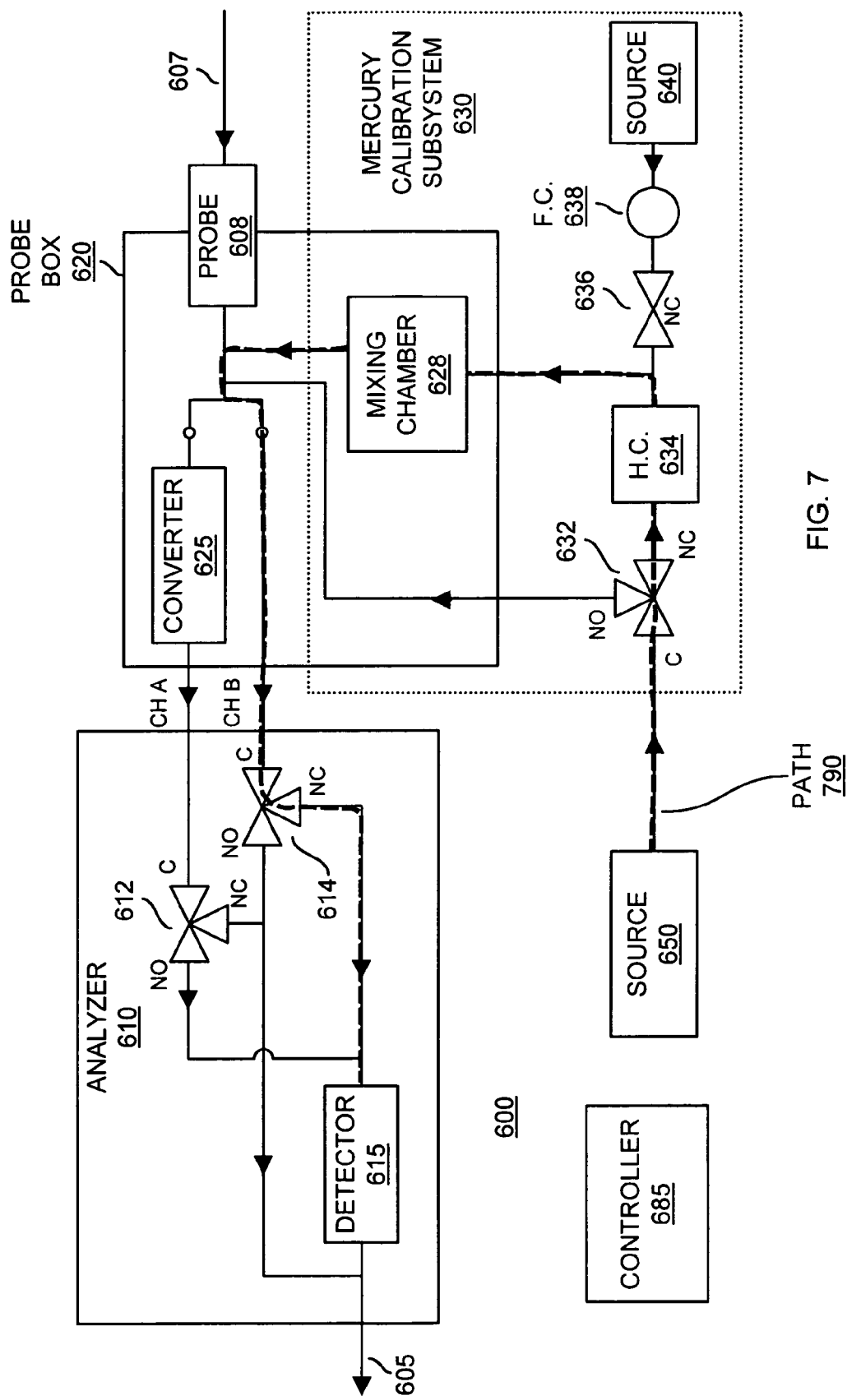

Note that a gas sample (whether from mercury calibration subsystem 630 or flue gas 607) can simultaneously flow through both channels A and B. However, during operation, only one of the channels is directed to pass the gas sample to the detector 615 while the other passes through analyzer 610 as exhaust 605 without passing through detector 615. The output of detector 615 also leaves the analyzer 610 as exhaust 605. In other words, while controller 685 sets valve 612 to direct a gas sample on channel A from input port C to output port NO, the controller 685 simultaneously sets valve 614 to direct the gas sample on channel B from input port C to output port NO. While in this mode setting (as shown in FIG. 6), the output of detector 615 and gas sample on channel B passing through valve 614 combine to form exhaust 605. Conversely, while controller 685 sets valve 612 to direct a gas sample on channel A from input port C to output port NC (bypassing detector 615), the controller simultaneously sets valve 614 to direct the gas sample on channel B from input port C to output port NC. While in this mode setting (as shown in FIG. 7), the output of detector 615 and gas sample on channel A passing through valve 612 combine to form exhaust 605.

Now more particularly, to direct an elemental mercury calibration gas sample from source mercury 650 (e.g., mercury vapor or gas) to detector 615 on flow path 690, the controller 685 sets valve 632 and valve 612 so that the gas sample flows through valve 632, humidity controller 634, mixing chamber 628, converter 625, and valve 612 to detector 615. Accordingly, controller 685 selectively delivers different gas samples (e.g., flue gas 607 or calibration gas samples from mercury calibration subsystem 630) along channels A and B to detector 615. According to one configuration, the controller 685 repeatedly switches between delivery of different gas samples on the first channel and the second channel to the detector to verify at least one of: i) an ability of the detector to detect elemental mercury gas, and ii) an ability of the converter to convert oxidized mercury into elemental mercury gas.

The humidity controller 634 disposed within subsystem 630 modifies (e.g., increases or decreases) a relative humidity of the calibration gas sample so that the relative humidity of a mercury gas sample is greater than 20%, such as within a specified range of between 50% and 80%. The corresponding temperature of gas sample at humidity controller 634 may be in the range of 15-35 degrees Celsius.

Humidifying (e.g., water vapor) to a mercury calibration gas sample enhances a flow of the gas sample (e.g., oxidized mercury) along a flow path. In other words, adjusting the relative humidity of the gas sample ensures that a majority of the elemental mercury and/or oxidized mercury in a gas sample does not stick to the walls of pipes, conduits, filters, etc. defining a flow path to detector 615. According to one configuration, the humidity controller 634 (e.g., a permeation wetter or dryer) includes a vessel of distilled water that removes or adds water to the gas sample.

Also, note that the humidity controller 634 can modify a relative humidity associated with a calibration gas sample to simulate a relative humidity of a flue gas 607 that is tested for presence of mercury. Accordingly, measurements associated with testing the flue gas 607 are more accurate because the mercury monitoring system 600 is calibrated under similar environmental conditions. In other words, the gas sample provided for calibration can be controlled to have a similar amount of water as that of a flue gas 607 under test.

As discussed above, probe box 620 of the mercury monitoring system 600 includes a converter 625 that converts any or most oxidized mercury gas (as by heating it to an elevated temperature such as 750 degrees Celsius) into elemental mercury gas. An output of the converter 625 in flow path 690 passes through valve 612 and feeds into the detector 615. Detector 615 detects an amount of elemental mercury gas in a received gas sample along flow path 690. In this example, the sample gas comes from source 650 such as a gas cylinder of elemental mercury of known concentration or a vapor generator which evaporates liquid mercury, either of which provides a known concentration of elemental mercury.

When flow path 690 is selected by controller 685 as shown in FIG. 6, the detector 615 detects a presence of a total amount of mercury in a gas sample from source 650 including i) an original amount of elemental mercury in the gas sample from source 650 as well as ii) any elemental mercury derived from conversion of oxidized mercury into elemental mercury by the converter 625. However, source 650 typically provides little or no oxidized mercury. (Recall that during any calibration test or any analysis of flue gas sample 607, the mercury monitoring system 600 can direct flow simultaneously through both channels A and B; typically, however, only the flow in one channel is directed into the detector 615—e.g., only the flow in channel B goes to detector 615 during operation per flow path 790 illustrated in FIG. 7.)

FIG. 7 illustrates a calibration flow path of the mercury monitoring system 600 according to embodiments herein. As shown, similar to the flow path 690 as discussed above in FIG. 6, flow path 790 of the mercury monitoring system 600 as shown in FIG. 7 also directs a gas sample from source 650 to the detector 615. However, flow path 790 (i.e., including channel B) bypasses the converter 625. Accordingly, if any oxidized mercury were present in the gas sample from source 650, it would not be converted into elemental mercury.

As discussed above, the mercury monitoring system 600 is at least occasionally calibrated (e.g., tested) with gas samples provided by the mercury calibration subsystem 630. For example, to calibrate the detector 615 of the mercury monitoring system 600, the mercury calibration subsystem 630 produces a gas sample from source 650 including a known concentration of elemental mercury gas with little or no oxidized mercury in the gas sample. The controller 685 of the mercury monitoring system 600 initiates switching between delivering the first gas sample from source 650 to the detector 615 on flow path 690 in FIG. 6 and flow path 790 in FIG. 7. Readings by the detector 615 for a gas sample received on flow path 690 and flow path 790 should be substantially the same because the gas sample includes little or no oxidized mercury.

The detector 615 is calibrated based on the readings for the gas sample received from the source 650 since the detector 615 should properly measure the known concentration of elemental mercury gas provided by the source 650. Note that calibration of the detector 615 can include hardware and/or software adjustments so that future readings of the detector accurately reflect how much elemental mercury is in a gas sample. According to one configuration, the detector 615 is a linear device and calibration at a single elemental mercury concentration is sufficient for proper operation. However, note that detector 615 can be calibrated at multiple different elemental mercury concentrations if necessary.

Assume that the source 650 provides a gas sample having a known concentration of gaseous elemental mercury of 10 micrograms per cubic meter. As shown by flow paths 690 and 790 respectively in FIGS. 6 and 7, the controller 685 repeatedly switches (e.g., approximately at one minute intervals) between channel A and channel B, and in both cases a concentration of gaseous elemental mercury of 10 micrograms per cubic meter is detected. Detector 615 can include an integrator circuit that is sampled one or more times during the one minute interval when the gas sample travels along a selected flow path. Upon switching to the other channel, the integrator associated with detector 615 is reset.

Figure 8:
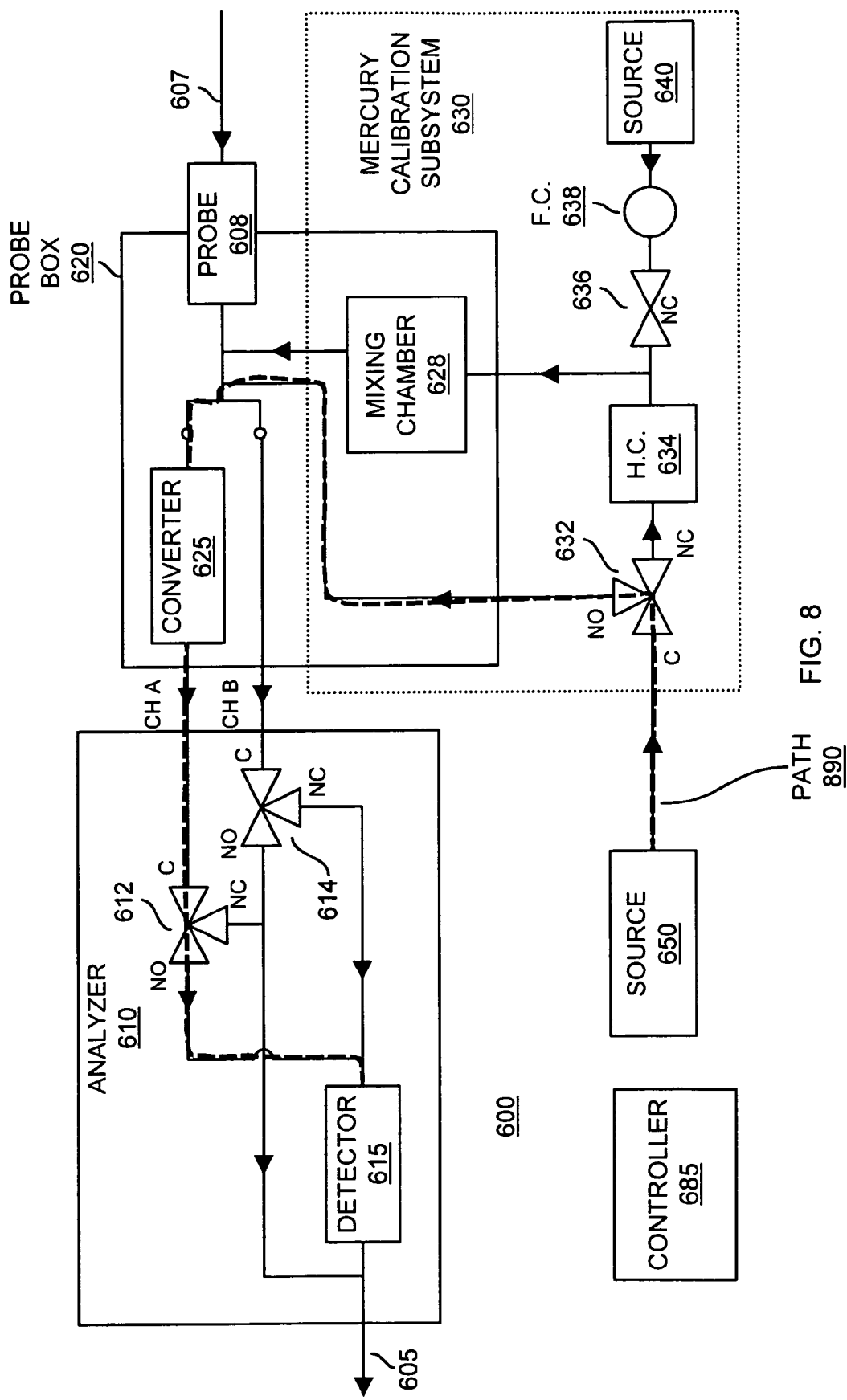
Figure 9:
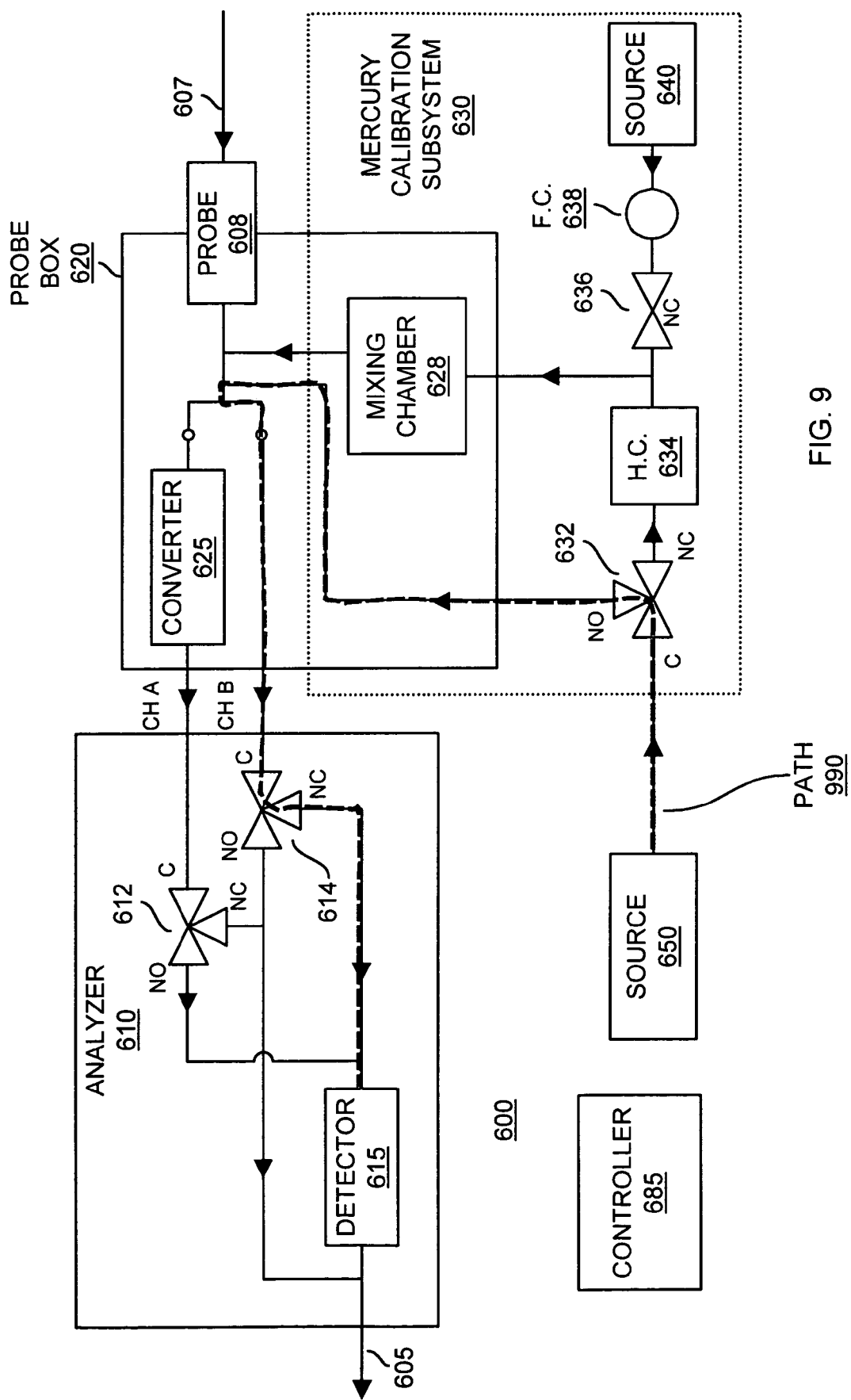

FIGS. 8 and 9 illustrate the same system 600 as in FIGS. 6 and 7 but operating with an alternate pair of flow paths in lieu of those shown in FIGS. 6 and 7, wherein mercury gases from source 650 flows to analyzer 610 without passing through humidity controller 634 and mixing chamber 628. For example, as shown in FIG. 8, the controller 685 can set valve 632 and valve 612 to direct a gas sample along flow path 890 from source 650 through valve 632, converter 625, and valve 612 to detector 615. As shown in FIG. 9, the controller 685 can set valve 632 and valve 614 to direct a gas sample along flow path 990 from source 650 through valve 632 and valve 614 to detector 615.

Assume that the source 650 provides a gas sample having a known concentration of gaseous elemental mercury of 10 micrograms per cubic meter as discussed above. As shown by flow paths 890 and 990 respectively in FIGS. 8 and 9, the controller 685 repeatedly switches (e.g., approximately every minute or so) between channels A and channel B and in both cases a known concentration of gaseous elemental mercury of 10 micrograms per cubic meter is detected. If necessary, the detector 615 is calibrated as discussed above in FIGS. 6 and 7.

Figure 10:
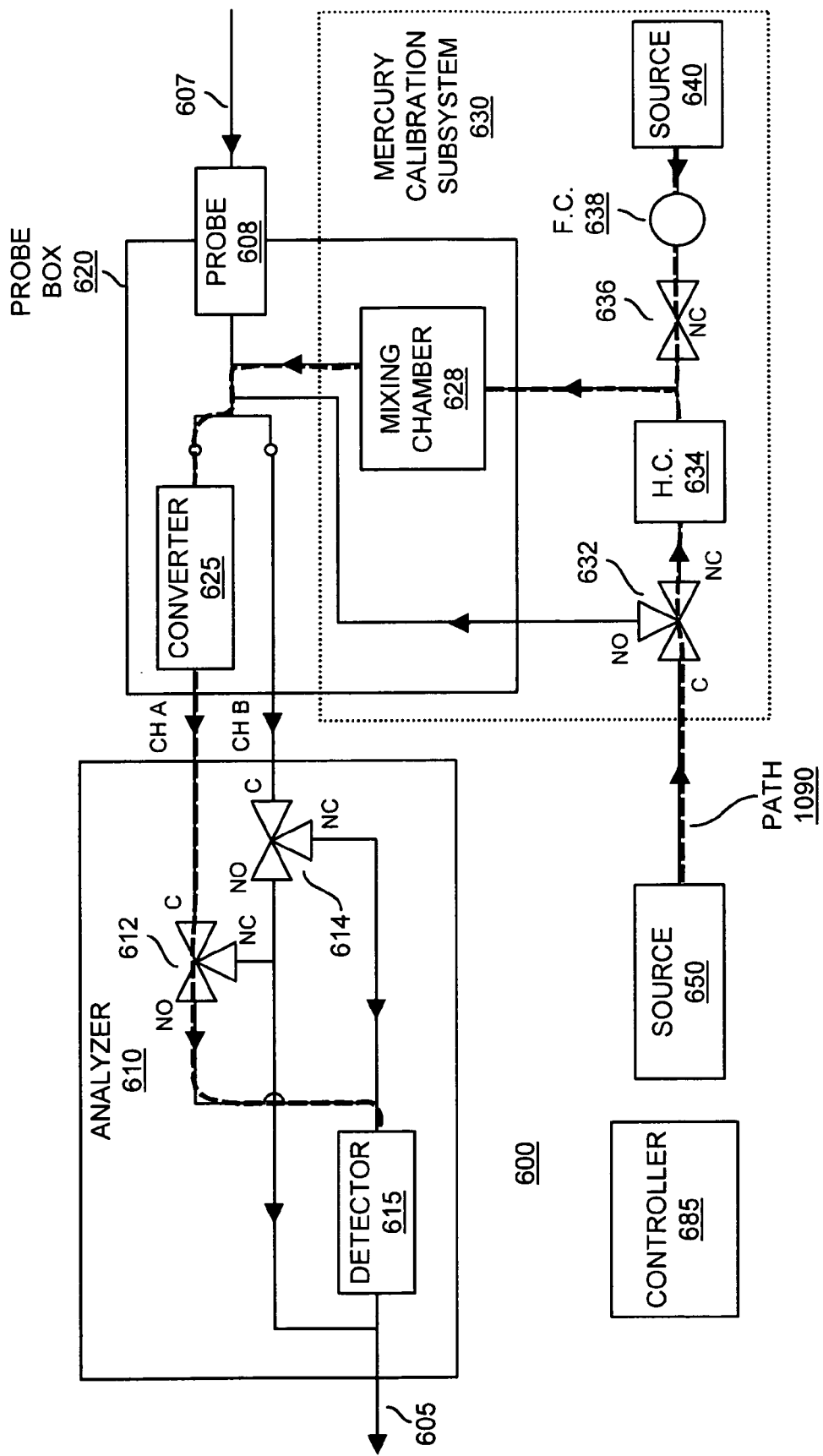
Figure 11:
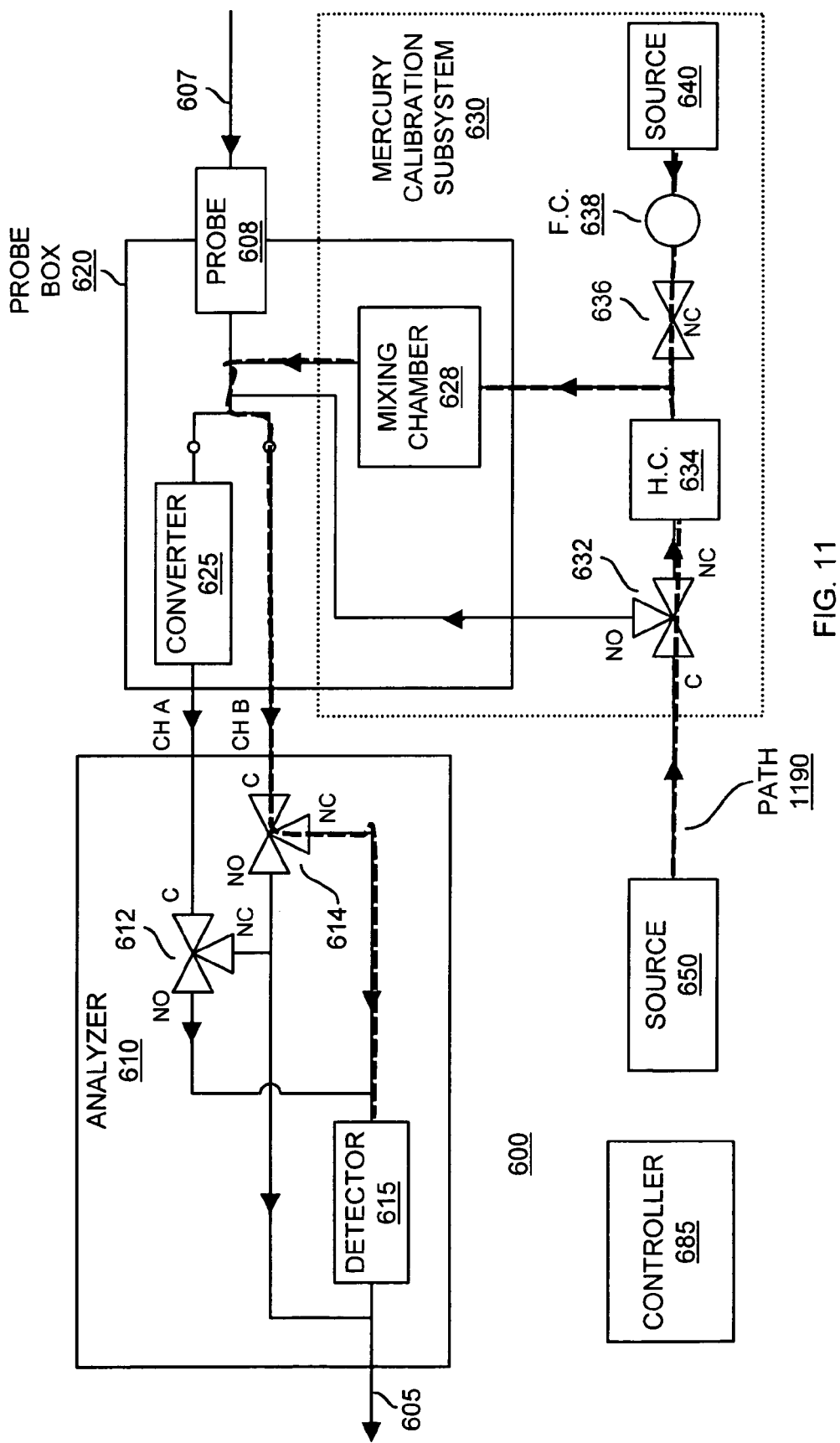

FIGS. 10 and 11 illustrate the system 600 operating with a pair of flow paths for testing response to oxidized mercury, including testing for a conversion efficiency associated with converter 625 according to embodiments herein. This efficiency test is generally performed after calibrating the detector 615 as mentioned above.

Figure 14:
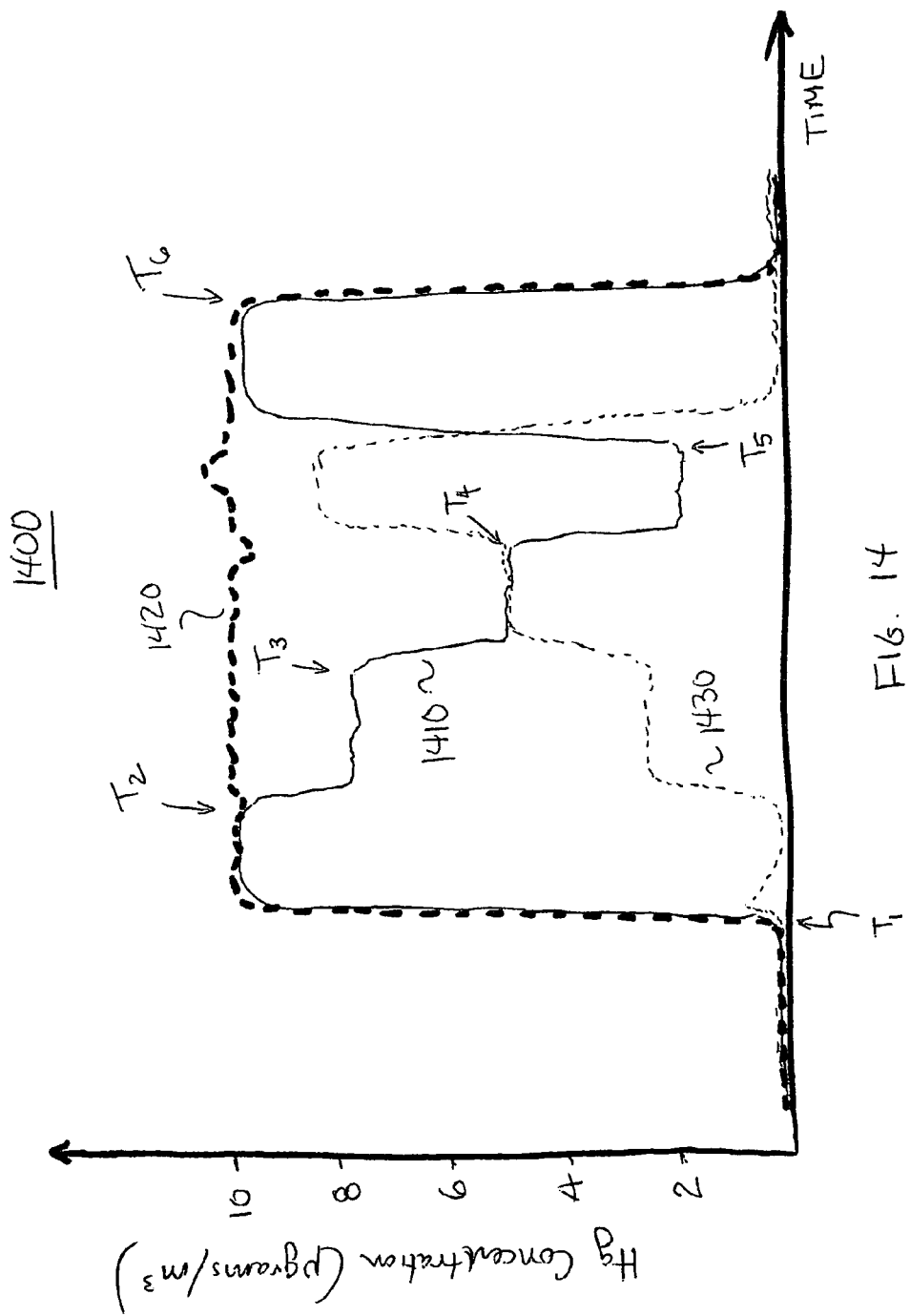
Figure 15:
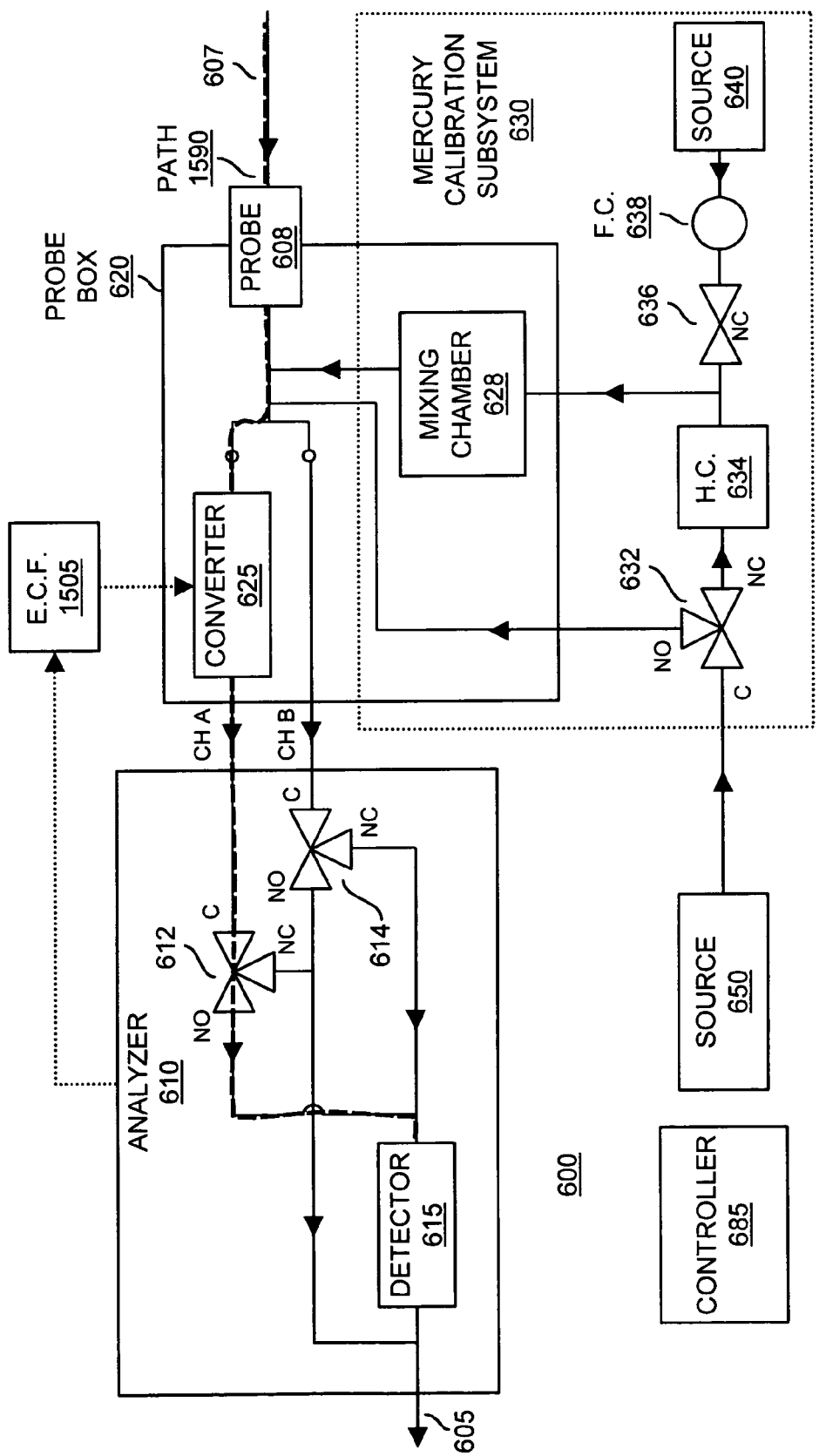

The efficiency of converter 625 can be occasionally tested to ensure its proper operation. Otherwise, the mercury monitoring system 600 and, more specifically, the detector 615 may not be able to measure the total mercury present in a flue gas 607 when so tested (as shown in FIGS. 14 and 15). As an example, a flue gas 607 under test may include a high level of oxidized mercury (e.g., mercury halide) and little or no elemental mercury. If the converter 625 does not efficiently (e.g., completely) convert substantially all of the mercury halide in the flue gas 607 to elemental mercury, then the detector 615 will be unable to accurately detect the total amount of mercury in the flue gas 607 sample. This measurement can be quite important because governmental standards require that a total amount of mercury present in a flue gas sample be maintained below a threshold value. Operating mercury monitoring system 600 with a faulty converter 615 (that does not properly convert oxidized mercury into elemental mercury) could violate this regulation.

To test the efficiency (e.g., an ability of the converter to convert oxidized mercury in the gas sample to elemental mercury) of the converter 615, the mercury calibration subsystem 630 produces gas sample in mixing chamber 628 (e.g., reaction chamber) by reacting elemental mercury gas received from source 650 with an oxidizing component received from source 640. Flow controller 638 and valve 636 control how much oxidizer gas is delivered to mixing chamber 628. Mixing chamber 628 can be heated to a temperature such around 400 degrees Celsius to enhance a conversion of elemental mercury gas into oxidized mercury (e.g. a mercury halide gas).

Recall that the elemental mercury gas received from source 650 can have a known concentration (e.g., 10 micrograms of mercury/cubic meter). The oxidizing component from source 640 preferably converts a portion of the known concentration of elemental mercury provided by source 650 into oxidized mercury gas such that the gas sample in mixing chamber 628 includes a mixture of an unknown concentration of elemental mercury gas and an unknown concentration of oxidized mercury gas. (Complete conversion of the elemental mercury in the gas sample to oxidized mercury is generally not desirable but could occur if the flow controller 638 were to pass an excessive amount of oxidizing agent through valve 636 to mixing chamber 628.)

The controller 685 of the mercury monitoring system 600 selectively switches between delivering the gas sample produced in mixing chamber 628 to detector 615 on flow path 1090 and flow path 1190 as shown respectively in FIG. 10 and FIG. 11. Similar to the technique as mentioned above, the controller 685 switches between flow paths to detector 615 at desired times such as every minute or so. An output of the detector 615 can feed into an integrator that is sampled at a rate such as every several seconds.

Periodically switching between receiving a gas sample at detector 615 from channel A and channel B (e.g., on flow paths 1090 and 1190) enables the mercury monitoring system 600 to continuously identify (e.g., on a continuous basis via use of the same detector) an amount of elemental mercury gas from source 650 as well as an amount of oxidized mercury gas produced in mixing chamber 628.

According to one configuration, an analyzer 610 of the mercury monitoring system 600 utilizes sample measurements from the detector 615 at appropriate times to measure an amount of original elemental mercury in the gas sample as received on channel B (e.g., flow path 1190 as shown in FIG. 11). After switching to receiving the gas sample on channel A (e.g., flow path 1090 as shown in FIG. 10), the analyzer 610 utilizes sample data from detector 615 to measure a total amount of mercury in the gas sample (rather than only the elemental mercury in the gas sample as on channel B) because the gas sample passes through converter 625, which converts any oxidized mercury into elemental mercury.

Based on repeated switching between channels and taking continuous measurements on channels A and B for a given gas sample produced in mixing chamber 628, the mercury monitoring system 600 can deduce how much oxidized mercury (e.g., mercury halide) is present in a gas sample. For example, while receiving a gas sample on channel B (e.g., flow path 1190 as shown in FIG. 11), the detector 615 measures an amount of elemental mercury in the gas sample. While receiving the gas sample on channel A (e.g., flow path 1090 as shown in FIG. 10), the detector 615 measures a total amount of mercury in the gas sample. The analyzer 610 of mercury monitoring system 600 deduces an amount of oxidized mercury in the gas sample based on a difference between the two measurements.

As briefly mentioned above, the mercury calibration subsystem 630 can include a flow controller 636 that controls a rate of flow of the oxidizing component received from source 640 to limit how much of the elemental mercury provided from gas source 650 is converted into the oxidized mercury gas in the mixing chamber 628. For example, the flow controller 638 can control and provide enough oxidizing component (e.g., a component such as chlorine, bromine, ozone, nitrate, etc.) to convert a portion of elemental mercury (e.g., an original concentration of 10 micrograms/cubic meter) from source 650 into oxidized mercury so that the output of the mixing chamber 628 contains approximately 25% elemental mercury and 75% oxidized mercury.

When this gas sample (e.g., assume that the gas from source 650 has a concentration of 10 micrograms of mercury/cubic meter) produced in mixing chamber 628 is switched between flow path 1090 and flow path 1190, the detector 615 should detect a presence of 2.5 micrograms/cubic meter on flow path 1190 and 10 micrograms/cubic meter on flow path 1090 since (ideally all of) the oxidized mercury in the gas sample from mixing chamber 628 will be converted into elemental mercury on the flow path 1090 (e.g., channel A). Thus, detector 615 measurements associated with flow path 1090 should indicate the total amount of mercury present in the gas sample.

If the detector 615 detects that the gas sample on flow path 1090 (e.g., the total mercury measurement channel which includes the converter 625) does not have an associated concentration of elemental mercury substantially equal to the known concentration of elemental mercury gas (e.g., 10 micrograms/cubic meter) initially in the gas sample as provided by source 650, then the converter 625 has failed to properly convert the oxidized mercury in the gas sample back to elemental mercury gas. If the error is less than a threshold value, the mercury monitoring system 600 produces and utilizes a correction factor for adjusting future measurements when sampling on channel A. In other words, if the reading of a total amount of elemental mercury on channel A is off by a fairly small amount, the mercury monitoring system 600 implements a correction factor to account for an inability to convert all oxidized mercury into elemental mercury. Otherwise, the converter 625 may be faulty and need to be replaced.

As an example, assume that the detector 615 measures the total mercury on channel A as 9.5 micrograms/cubic meter and an amount of elemental mercury of 2.5 micrograms/cubic meter on channel B. Recall that the reading on channel A should be 10 micrograms of mercury/cubic meter because this is the total amount of mercury in the gas sample. This means that the converter 625 likely only converted 7.0 micrograms/cubic meter of the oxidized mercury rather than all 7.5 micrograms/cubic meter in the gas sample. Thus, the efficiency of converter 625 (at this concentration) is 7/7.5 or 93.3%. The correction factor of 1.0714 (e.g., 1/0.9333) can be applied to future measurements in which the concentration of oxidized mercury is around 7.0 micrograms of mercury/cubic meter. For example, when measuring flue gas 607, if a measurement by detector 615 indicates a presence of 6.8 micrograms of mercury/cubic meter on channel A, the actual reading is more likely a concentration of (6.8×1.0714), or 7.285 micrograms of mercury/cubic meter due to the inability of the converter device to completely convert all oxidized mercury to elemental mercury in a respective gas sample.

Figure 12:
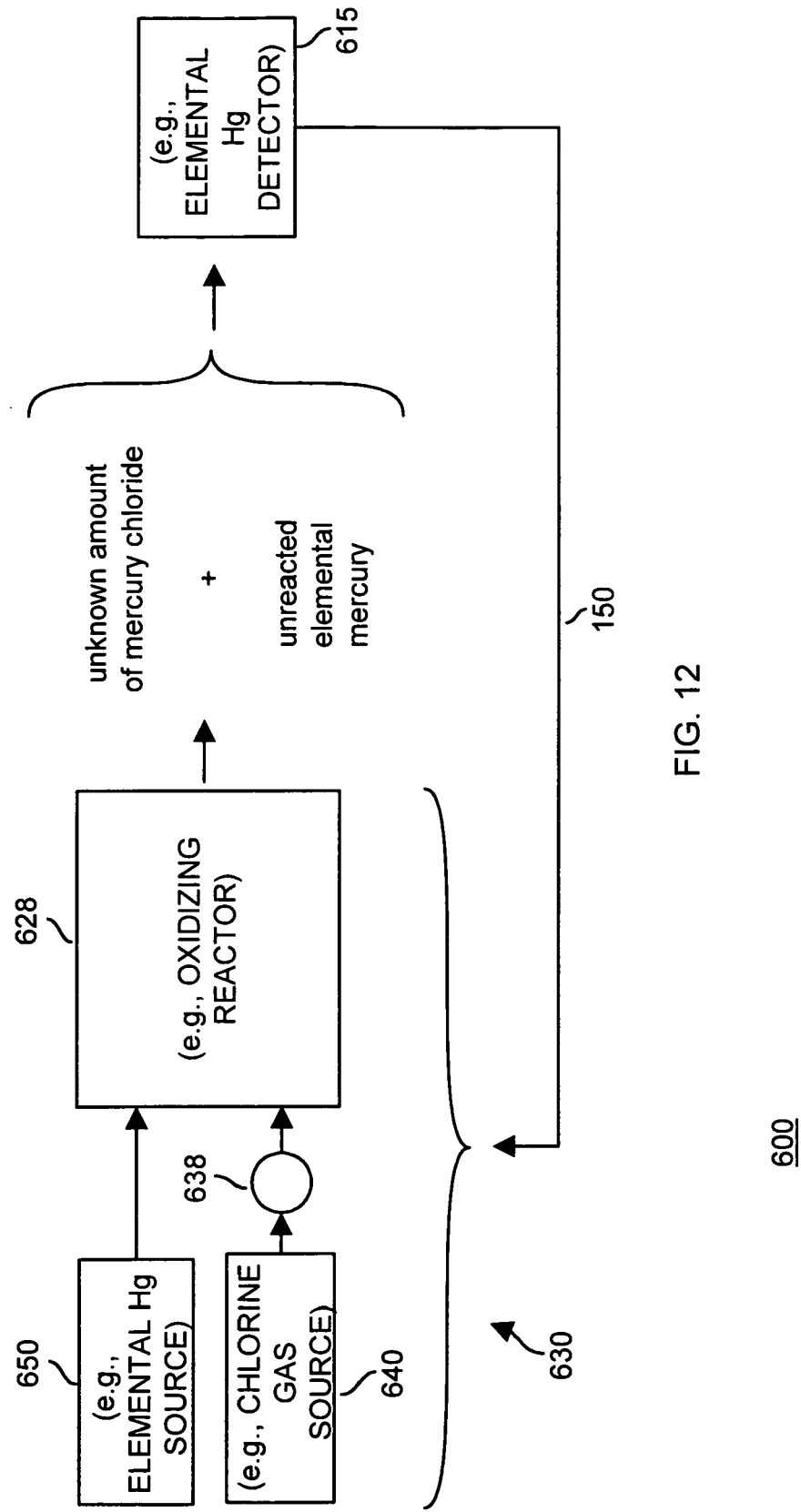
FIG. 12 is a diagram illustrating generation of a gas sample with oxidized mercury and elemental mercury for calibration, according to embodiments herein.

FIG. 12 is a diagram illustrating details of how mercury calibration subsystem 630 produces oxidized mercury for system calibration according to embodiments herein. The mercury calibration subsystem 630 for producing the mercury halide $HgCl_2$ includes an elemental mercury source (e.g., source 650) and a chlorine gas source (e.g., source 640) which feed mercury and chlorine vapors into a mixing chamber 628 (e.g., an oxidizing reactor). The mixing chamber 628 in turn produces an unknown amount of mercury chloride and an amount or remainder of un-reacted elemental mercury. For reasons explained below, one or more parameters such as the amount of chlorine directed to the mixing chamber 628 (e.g., oxidizing reactor) are adjusted via flow controller 638 so there is always an excess of elemental mercury leftover in the gas sample. Thus, the output of the reactor (mixing chamber 628) includes some amount of un-reacted elemental mercury (e.g., about 15-85% of the elemental mercury gas supplied from source 650). Making sure that a portion of the elemental mercury gas supplied from 650 is not converted into mercury halide can be accomplished by an automatic feedback mechanism 150, or manually, with any needed adjustments based on the amount of elemental mercury detected by detector 615.

To measure and control the amount of excess elemental mercury and to calculate, deduce or infer the unknown amount of $HgCl_2$ formed in the mixing chamber 628, the mercury monitoring system 600 includes a detector 615 and a computational device such as a computer, either within or separate from detector 615, to detect elemental mercury. In particular, elemental mercury detector 615 measures the amount of un-reacted elemental mercury output from mixing chamber 628 on channel B as discussed above. The detector 615 also measures the total amount of elemental mercury (i.e., the mercury provided by the source 650) by use of a bypass channel (channel A) through which the output of mixing chamber 628 is (periodically) passed and which includes a converter 625 to convert oxidized mercury to elemental mercury as previously discussed.

The difference between the known concentration of elemental mercury provided by the elemental mercury source 650 (known initially from parameters of the source 650 and/or measured by the detector 615 from the output of channel A) and the measured amount of un-reacted elemental mercury output from mixing chamber 628 indicates how much mercury chloride was produced in the mixing chamber 628. In other words, the amount of mercury chloride produced is based on post-reaction detection and analysis and is unknown until then. This deduced or estimated amount of mercury chloride sample is used for calibrating the mercury monitoring system 600 for oxidized mercury.

According to one configuration, the mercury monitoring system 600 intentionally does not completely oxidize all elemental mercury supplied to the mixing chamber 628, for at least two reasons: i) an indirect determination of oxidized mercury by subtraction provides a better representation and control of the oxidized mercury produced, and ii) to assure oxidation of all mercury would require an excessive amount of chlorine, and the excess chlorine might subsequently react with (re-oxidize) elemental mercury in the bypass channel or elsewhere in the system and interfere with accurate detection of elemental mercury. (Excess chlorine could be removed or scrubbed by a filter, but even then its presence would present a risk of breakthrough and/or a reduction in useful filter life.)

As indicated earlier, the mercury monitoring system 600 can include control, either manually or by a feedback loop 150, to ensure that only a portion (e.g., about 10-90%) of elemental mercury supplied by source 650 to the mixing chamber 628 is converted into mercury chloride. Thus, if the calculated amount of mercury chloride is below a target value, system parameter settings can be modified (e.g., to increase the amount of chlorine gas provided by source 640, raise a temperature of mixing chamber 628, etc.) so as to increase the amount of elemental mercury converted into mercury chloride. Conversely, if more than a desired amount of elemental mercury is being converted into mercury chloride in mixing chamber 628, system parameter settings of mercury monitoring system 600 can be modified (e.g., to decrease an amount of chlorine gas provided by source 640, decrease a temperature of mixing chamber 628, control a flow using valve 638, etc.) to reduce the amount of conversion.

Figure 13:
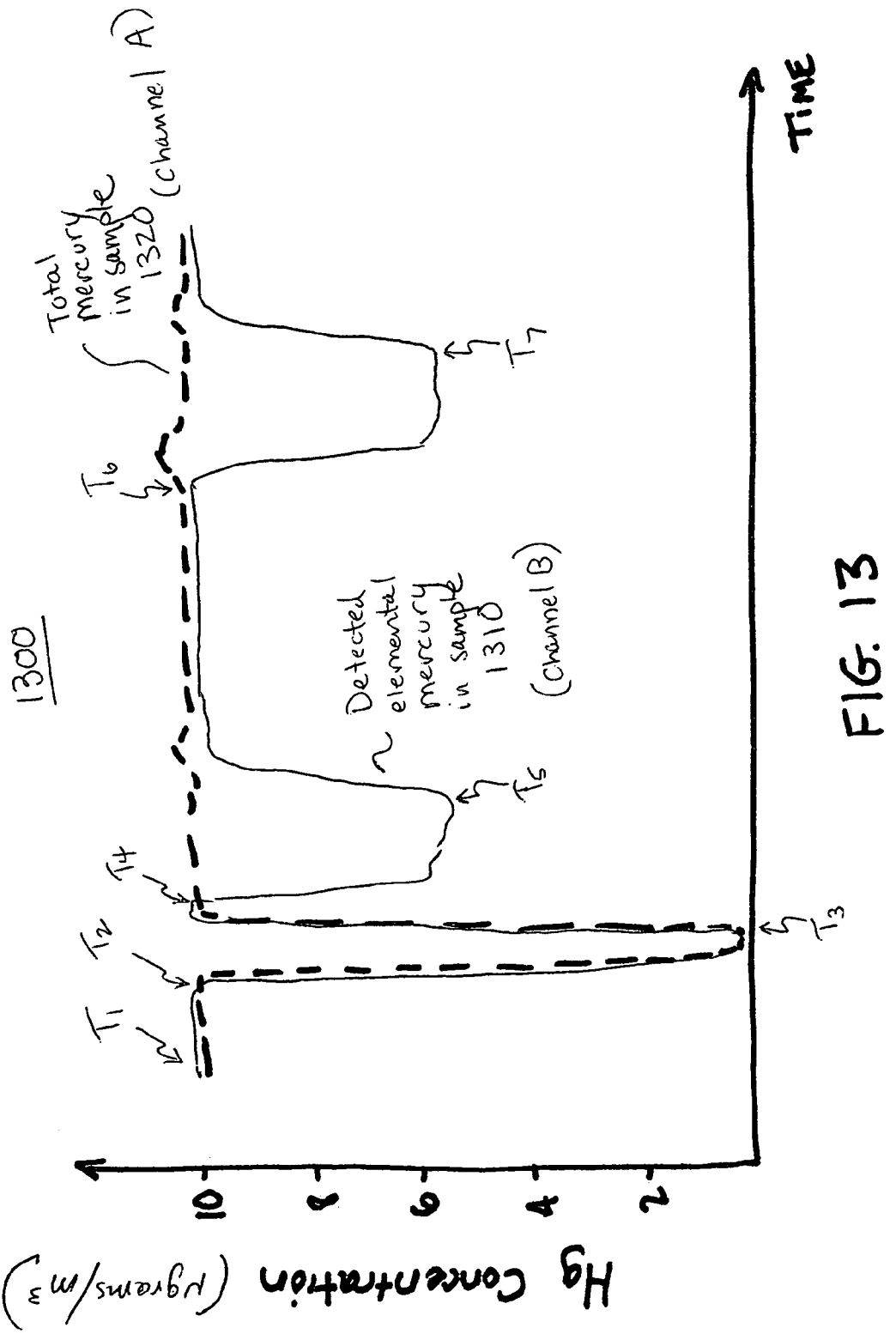
FIGS. 13 and 14 are graphs illustrating detection of elemental mercury and total mercury in a gas sample according to embodiments herein.

FIG. 13 is a graph 1300 illustrating hypothetical results associated with testing of a mercury monitoring system 600 according to embodiments herein. Graph 1300 represents a display of measurements produced by detector 615 while switching between detecting elemental mercury in flow path 1090 (as shown in FIG. 10) and flow path 1190 (as shown in FIG. 11) over time. Plot 1310 on graph 1300 represents the detected elemental mercury in a sample received on channel B as detected by detector 615. Plot 1320 on graph 1300 represents the detected total elemental mercury in a sample received on channel A as detected by detector 615. A time difference between time T1 and time T2 or between T1 and T6 can be on the order of a half hour. During this time span, controller 685 of mercury monitoring system 600 controls valves (e.g., valve 612, valve 614, valve 632, and valve 636) and flow controller 638 as follows:

i) At time T1, the controller 685 enables a flow of elemental mercury gas (e.g., a known concentration of 10 micrograms/cubic meter) from source 650 through mixing chamber 628 to detector 615 on flow path 1090 and flow path 1190. Source 640 is disabled from providing an oxidizing gas by shutting off valve 636. Between time T1 and T2, both channel A and channel B measure the same level of approximately 10 micrograms/cubic meter of elemental mercury in the gas sample.

ii) At time T2, the controller 685 disables a flow of elemental mercury gas (e.g., a known concentration of 10 micrograms/cubic meter) from source 650 through mixing chamber 628 to detector 615 on flow paths 1090 and 1190. Source 650 is disabled from providing mercury gas by shutting off valve 632. Between time T2 and T3, both channel A and channel B eventually measure no elemental mercury in the calibration gas sample.

iii) At time T3, the controller 685 re-enables a flow of elemental mercury gas (e.g., a known concentration of 10 micrograms/cubic meter) from source 650 through 632 and mixing chamber 628 to detector 615 on flow paths 1090 and 1190. Source 640 is disabled from providing an oxidizing gas by shutting off valve 636. Between time T3 and T4, both channel A and channel B eventually measure the same level of approximately 10 micrograms/cubic meter of elemental mercury in the gas sample again.

iv) At time T4, the controller 685 continues to enable a flow of elemental mercury gas (e.g., a known concentration of 10 micrograms/cubic meter) from source 650 through mixing chamber 628 to detector 615. The controller 685 controls valve 636 and flow controller 638 to enable source 640 to provide enough oxidizing gas to convert about 40% of the elemental mercury gas in mixing chamber 628 (as provided by source 650) into oxidized mercury (e.g., mercury chloride). Between time T4 and T5, the controller 685 controls the valves in mercury monitoring system 600 to switch between measuring a level of elemental mercury in the sample gas from channel A and channel B as previously discussed. Between time T4 and T5, plot 1320 of graph 1300 reflects that the total amount of elemental mercury received on channel A remains approximately constant. Between time T4 and T5, plot 1310 of graph 1300 reflects that the amount of elemental mercury gas in the sample as received on channel B decreases as a result of a conversion of elemental mercury from source 650 into oxidized mercury.

v) At time T5, the controller 685 continues to enable a flow of elemental mercury gas (e.g., a known concentration of 10 micrograms/cubic meter) from source 650 through mixing chamber 628 to detector 615. The controller 685 controls valve 636 and flow controller 638 to disable source 640 from delivering oxidizing gas to mixing chamber 628. Accordingly, between time T5 and T6, none of the gas from source 650 is converted into oxidized mercury, and thereafter until time T6 as shown by plots 1310 and 1320, both elemental mercury readings on channel A and channel B measure the same level of approximately 10 micrograms/cubic meter of elemental mercury in the gas sample.

vi) At time T6, the controller 685 continues to enable a flow of elemental mercury gas (e.g., a known concentration of 10 micrograms/cubic meter) from source 650 through mixing chamber 628 to detector 615. The controller 685 controls valve 636 and flow controller 638 to again enable source 640 to provide enough oxidizing gas to convert about 40% of the elemental mercury gas in mixing chamber 628 (as provided by source 650) into oxidized mercury (e.g., mercury chloride). Between time T6 and T7, the controller 685 controls the valves in mercury monitoring system 600 to switch between measuring a level of elemental mercury in the sample gas from channel A and channel B as previously discussed. Between time T6 and T7, plot 1320 of graph 1300 reflects that the total amount of elemental mercury received on channel A remains approximately constant. Between time T6 and T7, plot 1310 of graph 1300 again reflects that the amount of elemental mercury gas in the sample as received on channel B decreases as a result of a conversion of elemental mercury from source 650 into oxidized mercury.

vii) At time T7, the controller 685 continues to enable a flow of elemental mercury gas (e.g., a known concentration of 10 micrograms/cubic meter) from source 650 to detector 615. The controller 685 controls valve 636 to disable source 640 from delivering oxidizing gas to mixing chamber 628. Accordingly, eventually none of the gas in mixing chamber 628 from source 650 is converted into oxidized mercury. As shown by plots 1310 and 1320 after time T7, both elemental mercury readings on channel A and channel B eventually measure the same level of approximately 10 micrograms/cubic meter of elemental mercury in the gas sample.

Additional embodiments herein include verifying efficiency of the converter 625 over a range of different concentrations of oxidized mercury. Note that an ideal converter device will be able to convert 100% of the oxidized mercury into elemental mercury gas regardless of the concentration of oxidized mercury. However, efficiency of converter 625 often varies depending on concentration of the oxidized mercury to be converted. Based on sampling of gases having different concentrations of oxidized mercury at different times, the mercury monitoring system 600 as discussed herein can identify appropriate correction factors to apply for different detected concentrations for more accurately determining actual concentrations of oxidized mercury in a flue gas sample.

As illustrated in the graph 1400 of FIG. 14 illustrating hypothetical operation, the mercury calibration subsystem 630 produces multiple different sample gases having different concentrations of oxidized mercury and elemental mercury for testing converter efficiency. Plot 1410 of graph 1400 represents measurements of an amount of elemental mercury in a gas sample as detected on channel B. Plot 1420 of graph 1400 represents measurements of total elemental mercury detected in the gas sample on channel A. Plot 1430 of graph 1400 represents a deduced amount of oxidized mercury present in the different gas samples produced by mercury calibration subsystem 630. The time span between time T1 and T6 represents a testing cycle of approximately a half hour to an hour of time. This can vary depending on the application. Recall again that controller 685 switches between delivery of sample gases in mixing chamber 628 on channels A and B to detector 615 each minute or so. The analyzer 610 can be configured to initiate operation of the detector 615 at multiple sample times during the test duration between T1 and T6 to test an ability of the converter to convert the different concentration levels of oxidized mercury in the gas sample into elemental mercury for each of the steps.

For example, similar to the techniques as discussed above in FIG. 13, the controller 685 of mercury calibration subsystem 630 controls a flow rate (via flow controller 638) of oxidizing component from source 640 for a first time duration between time T2 and time T3 so that the output of mixing chamber 628 includes a first set of concentrations of elemental mercury gas and oxidized mercury gas (e.g., 25% oxidized mercury and 75% elemental mercury). As discussed above, for this first time duration, the controller 685 switches between delivering the gas sample produced in mixing chamber 628 to the detector 615 on channel A (e.g., flow path 1090) and channel B (e.g., flow path 1190) to identify an amount of elemental mercury and oxidized mercury present in the gas sample.

Based on measurements by the detector on channel A and channel B, the analyzer 610 of mercury monitoring system 600 utilizes sample data produced by detector 615 to identify whether converter 625 efficiency falls below 100% for the given concentration of oxidized mercury (e.g., 25% oxidized mercury or 2.5 micrograms/cubic meter) in the gas sample. If necessary, the mercury monitoring system 600 or, more specifically, the analyzer 610 produces a correction factor associated with the converter device for the given concentration level so that future measurements of elemental mercury received on channel A are more accurate.

After testing the first gas sample (e.g., 25% oxidized mercury to 75% elemental mercury) for the first time duration between time T2 and time T3, the mercury calibration subsystem 630 controls a flow rate of oxidizing component from source 640 so that the output of mixing chamber 628 includes a second set of concentrations of elemental mercury gas and oxidized mercury gas (e.g., 50% oxidized mercury and 50% elemental mercury) for a second duration of time between time T3 and time T4. For this second time duration, the mercury monitoring system 600 switches between delivering the gas sample on channel A and channel B to the detector 615 so that the analyzer 610 can identify an amount of elemental mercury and oxidized mercury present in the second gas sample. Based on measurements by the detector 615, the mercury monitoring system 600 identifies whether converter efficiency falls below 100% for the given concentration of oxidized mercury (e.g., 5 micrograms/cubic meter) in the gas sample. If necessary, the analyzer 610 of mercury monitoring system produces a correction factor associated with the converter device for this concentration level.

After testing the second gas sample (e.g., 50% oxidized mercury to 50% elemental mercury) for the second time duration between time T3 and time T4, the mercury calibration subsystem 630 controls a flow rate of oxidizing component from source 640 so that the output of mixing chamber 628 includes a third set of concentrations of elemental mercury gas and oxidized mercury gas (e.g., 75% oxidized mercury to 25% elemental mercury) for a third duration of time between time T4 and time T5. For this third time duration, the mercury monitoring system 600 switches between delivering the gas sample on channel A and channel B to the detector 615 (as previously discussed) to identify an amount of elemental mercury and oxidized mercury present in the third gas sample. Based on measurements by the detector 615 during the third time duration, the mercury monitoring system 600 identifies whether converter efficiency falls below 100% for the given concentration of oxidized mercury (e.g., 7.5 micrograms/cubic meter) in the gas sample. If necessary, the mercury monitoring system produces a correction factor associated with the converter device for this concentration level.

Although graph 1400 illustrates three different testing ratios to check an efficiency associated with converter 625, note that any number of different sample gases including different ratios of elemental mercury gas to oxidized mercury gas can be used to verify the efficiency of the converter 625 over a range of different oxidized mercury concentrations.

Figure 16:
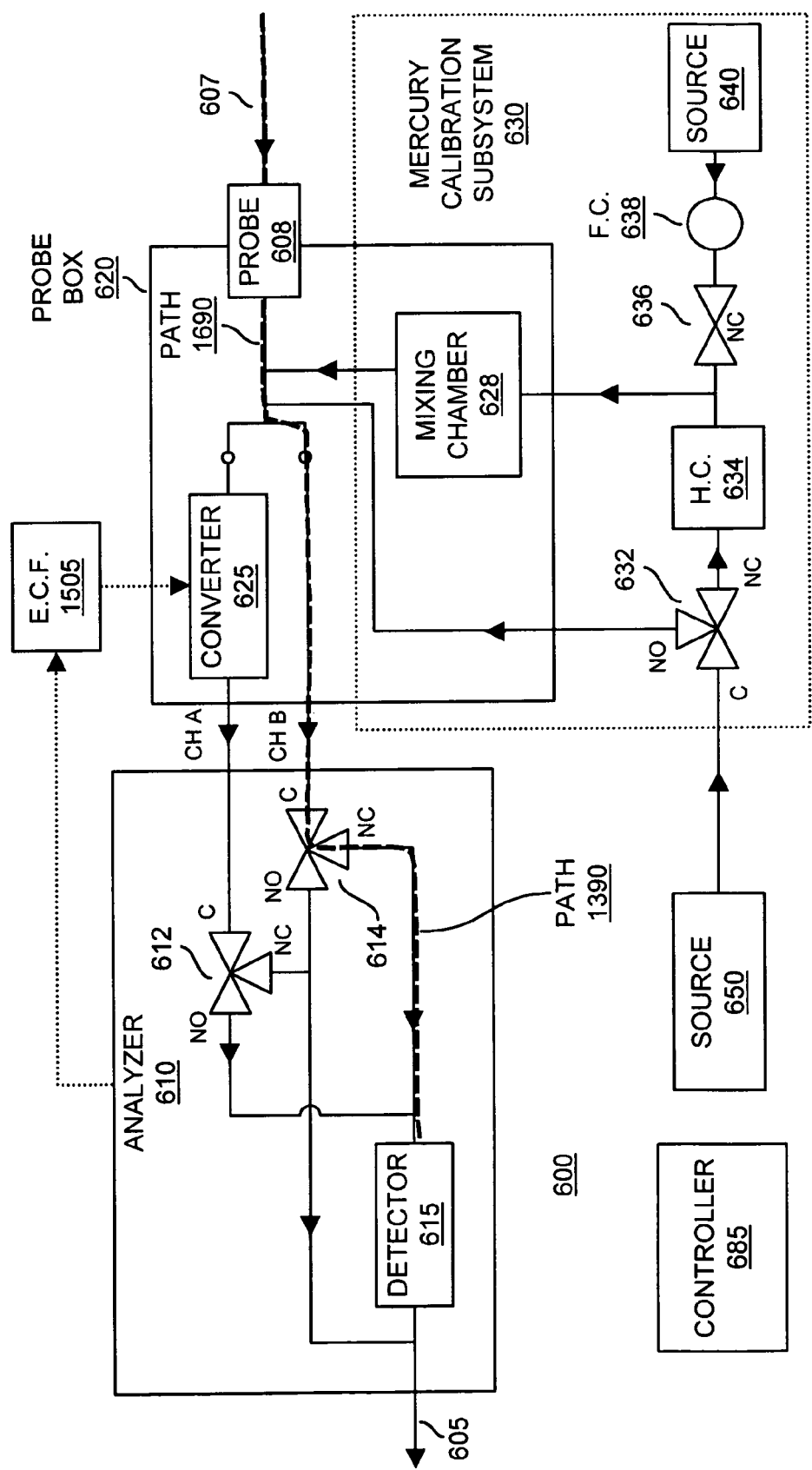

Passing the above integrity checks (e.g., detector calibration and converter efficiency) provides an assurance that the mercury monitoring system can properly detect mercury in a flue gas 607 sample. FIGS. 15 and 16 illustrate respective flow paths 1590 and 1690 in the mercury monitoring system 600 to measure a total amount of mercury present in the flue gas 607 (e.g., via a measurement on channel A or flow path 1590) and an amount of elemental mercury present in the flue gas 607 (e.g., via a measurement on channel B or flow path 1690). The techniques discussed above disclose how to produce different efficiency correction factors 1505. The different efficiency correction factors 1505 can be used to more accurately indicate a total amount of mercury present in a flue gas 607 sample.

For example, based on testing as discussed above, suppose that the converter 625 is: i) 98% efficient at converting oxidized mercury into elemental mercury for a concentration of 2.5 micrograms of mercury/cubic meter, ii) 97% efficient at converting oxidized mercury into elemental mercury for a concentration of 5.0 micrograms of mercury/cubic meter, and iii) 93% efficient at converting oxidized mercury into elemental mercury for a concentration of 7.5 micrograms of mercury/cubic meter. The corresponding efficiency correction factors would be 1.02, 1.03, and 1.08 for the different concentrations. In furtherance of the present example, via use of detector 615 and switching between measurements on channel A and channel B, suppose that the mercury monitoring system 600 detects a concentration of 5.6 micrograms/cubic meter of oxidized mercury and a concentration of 2.7 micrograms/cubic meter in flue gas 607. The efficiency correction factor of 1.03 is multiplied by 5.6 in order to identify an actual amount of oxidized mercury in the flue sample 607. The total mercury in the flue gas 607 would be (5.768+2.7) or 8.468 instead of (5.6+2.7), or 8.3 micrograms of mercury/cubic meter.

According to one configuration, a linear correction factor (as opposed to non-linear correction via application of different correction factors as discussed above for different ranges) such as a correction factor of 1.05 can be applied to all ranges of concentrations. This simplifies the conversion process because there is no need to determine a particular correction factor to be used for a given concentration range.

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. A method comprising:
   providing a gas sample for calibrating a mercury monitoring system;
   initiating application of a first mode of the mercury monitoring system for delivering the gas sample on a first flow path through a converter to a detector operable to measure concentrations of elemental mercury gas in the gas sample, the converter operable to convert oxidized mercury in the gas sample into elemental mercury gas; and
   initiating application of a second mode of the mercury monitoring system for delivering the gas sample to the detector via a second flow path that bypasses the converter.

2. A method as in claim 1 further comprising:
   repeatedly switching between application of the first mode and the second mode to verify at least one of: i) an ability of the detector to detect elemental mercury gas, and ii) an ability of the converter to convert oxidized mercury into elemental mercury gas.

3. A method as in claim 1, wherein providing the gas sample includes producing the gas sample to have a known concentration of gaseous elemental mercury, the method further comprising:
   repeatedly switching between application of the first mode and the second mode to calibrate the detector by exposing the detector to the known concentration of gaseous elemental mercury in the gas sample.

4. A method as in claim 1 further comprising:
   prior to delivery of the gas sample on the first flow path or the second flow path, converting a portion of elemental mercury in the gas sample to oxidized mercury; and
   repeatedly switching between i) initiating delivery of the gas sample on the first flow path through the converter to the detector and ii) initiating delivery of the gas sample to the detector via a second flow path that bypasses the converter in order to test an ability of the converter to convert oxidized mercury in the gas sample to elemental mercury.

5. A method as in claim 1, wherein providing the gas sample includes:
   modifying a relative humidity of gas used to produce the gas sample in order to enhance a flow of the gas sample along the first flow path and the second flow path.

6. A method as in claim 1, wherein providing the gas sample includes:
   receiving elemental mercury gas from an elemental mercury gas source;
   modifying a relative humidity level of the elemental mercury gas;
   receiving an oxidizing component from an oxidizing component source; and
   mixing the elemental mercury gas with the oxidizing component in a mixing chamber to produce the gas sample.

7. A method as in claim 1, wherein providing the gas sample includes:
   modifying a relative humidity associated with the gas sample in order to simulate a relative humidity of flue gas that is tested for presence of mercury after calibration of the detector and the converter with the gas sample.

8. A method as in claim 1, wherein providing the gas sample includes producing the sample by:
   receiving an elemental mercury gas of known concentration;
   controlling how much of the delivered elemental mercury gas of known concentration is converted into oxidized mercury such that the provided gas sample includes different concentrations of elemental mercury over a test duration.

9. A method as in claim 1, wherein providing the gas sample includes producing the gas sample to have different concentrations of oxidized mercury over time.

10. A method as in claim 1, wherein providing the gas sample includes:
    producing the gas sample by reacting elemental mercury gas received from a first source with an oxidizing component received from a second source, the oxidizing component converting a portion of the elemental mercury from the first source into oxidized mercury gas such that the gas sample selectively delivered on the first flow path and the second flow path includes a mixture of an unknown concentration of elemental mercury gas and an unknown concentration of oxidized mercury gas.

11. A method as in claim 10 including determining the concentration of oxidized mercury gas produced from the reaction of the oxidizing component with the elemental mercury received from the first source by computing the difference between the concentrations of elemental mercury gas measured by the detector receiving the gas sample selectively delivered on the first and second flow paths, respectively.

12. A method as in claim 11, wherein producing the gas sample includes:
    controlling a flow of the oxidizing component received from the second source to limit the amount of the elemental mercury provided from the first source that is converted into the oxidized mercury gas.

13. A method as in claim 11, wherein producing the gas sample includes:

for a first time duration, controlling a flow rate of the oxidizing component received from the second gas source so that the gas sample produced includes a first concentration of oxidized mercury gas; and for a second time duration, controlling a flow rate of the oxidizing component received from the second gas source so that the gas sample produced includes a second concentration of oxidized mercury gas.

14. A method as in claim 13 further comprising:

for the first and second time durations, switching between application of the first mode and the second mode and determining the concentrations of oxidized mercury present in the gas sample.

15. A method as in claim 1 further comprising:

testing efficiency of the converter in the first flow path by:
starting with a known concentration of elemental mercury gas initially in the gas sample;
converting a portion of the elemental mercury in the gas sample to oxidized mercury such that the gas sample includes an unknown concentration of elemental mercury and an unknown concentration of oxidized mercury;
delivering the gas sample including the unknown concentration of elemental mercury and an unknown concentration of oxidized mercury along the first flow path to the detector; and
verifying whether the detector detects that the delivered gas sample has a concentration of elemental mercury substantially equal to the known concentration of elemental mercury gas initially in the gas sample.

16. A method as in claim 15 further comprising:

if the detector does not detect that the delivered gas sample has a concentration of elemental mercury substantially equal to the known concentration of elemental mercury gas initially in the gas sample, determining a correction factor for adjusting future measurement readings provided by the detector when sampling on the first flow path.

17. A method as in claim 1, wherein providing the gas sample includes:

controlling a flow rate of delivering an oxidizing component to a mixing chamber so that the mixing chamber produces the gas sample to have different concentrations of oxidized mercury gas over a test duration.

18. A method as in claim 17 further comprising:

initiating operation of the detector at multiple sample times during the test duration to test an ability of the converter to convert the different concentrations of oxidized mercury in the gas sample into elemental mercury.

19. A mercury monitoring system comprising:

a mixing chamber configured to produce a gas sample;
a detector configured to measure concentrations of elemental mercury gas in the gas sample;
a first channel from the mixing chamber to the detector, the first channel including a converter operable to convert oxidized mercury in the gas sample into elemental mercury gas;
a second flow channel from the mixing chamber to the detector, bypassing the converter; and
a controller configured to selectively deliver the gas sample from the mixing chamber along the first channel and second channel to the detector.

20. A mercury monitoring system as in claim 19, wherein the controller is configured to repeatedly switch between delivery of the gas sample on the first channel and the second channel to the detector to verify at least one of: i) an ability of the detector to detect elemental mercury gas, and ii) an ability of the converter to convert oxidized mercury into elemental mercury gas.

21. A mercury monitoring system as in claim 19, wherein the controller is configured to control sources providing input to the mixing chamber such that the gas sample from the mixing chamber includes a known concentration of gaseous elemental mercury; and wherein the controller is configured to repeatedly switch between delivery of the gas sample on the first channel and the second channel to calibrate the detector by exposing the detector to the known concentration of gaseous elemental mercury in the gas sample.

22. A mercury monitoring system as in claim 19, wherein the mixing chamber is configured to convert a portion of received elemental mercury gas into oxidized mercury gas to produce the gas sample; and wherein the controller is configured to repeatedly switch between i) initiating delivery of the gas sample on the first channel through the converter to the detector, and ii) initiating delivery of the gas sample to the detector via the second channel that bypasses the converter in order to test an ability of the converter to convert oxidized mercury in the gas sample to elemental mercury.

23. A mercury monitoring system as in claim 19 further comprising:

a humidifier configured to modify a relative humidity of elemental mercury gas provided to the mixing chamber for producing the gas sample.

24. A mercury monitoring system as in claim 19 further comprising:

an elemental mercury gas source;
an oxidizing component source;
a humidifier to modify a relative humidity level of elemental mercury gas delivered from the elemental mercury gas source; and
wherein the mixing chamber is configured to produce the gas sample based on reaction of an oxidizing component received from the oxidizing component source and elemental mercury gas received from the elemental mercury source through the humidifier.

25. A method as in claim 19, wherein the mixing chamber is configured to receive an elemental mercury gas of known concentration; and wherein the controller is configured to control how much of the received elemental mercury gas of known concentration is converted into oxidized mercury such that the gas sample produced by the mixing chamber includes different concentrations of elemental mercury over a test duration.

26. A mercury monitoring system as in claim 19, wherein the mixing chamber is configured to produce the gas sample by reacting elemental mercury gas received from a first source with an oxidizing component received from a second source, the oxidizing component converting a portion of the elemental mercury from the first source into oxidized mercury gas such that the gas sample selectively delivered by the controller on the first channel and the second channel includes a mixture of an unknown concentration of elemental mercury gas and an unknown concentration of oxidized mercury gas.

27. A mercury monitoring system as in claim 26 further comprising:

an analyzer configured to determine a concentration of oxidized mercury gas produced from a reaction, in the mixing chamber, of the oxidizing component received from the second source with the elemental mercury received from the first source by computing the difference between concentrations of elemental mercury gas measured by the detector on the first channel and second channel, respectively.

28. A mercury monitoring system as in claim 27, wherein the controller is configured to produce the gas sample in the mixing chamber by controlling a flow of the oxidizing component received by the mixing chamber from the second source to limit the amount of the elemental mercury provided from the first source that is converted into the oxidized mercury gas.

29. A mercury monitoring system as in claim 27, wherein the controller is configured to:
   for a first time duration, control a flow rate of the oxidizing component received from the second gas source so that the gas sample includes a first concentration of oxidized mercury gas; and
   for a second time duration, control a flow rate of the oxidizing component received from the second gas source so that the gas sample includes a second concentration of oxidized mercury gas.

30. A mercury monitoring system as in claim 19, wherein the mixing chamber is configured to:
   receive elemental mercury gas of known a known concentration;
   convert a portion of the received elemental mercury gas to oxidized mercury gas such that the gas sample from the mixing chamber includes an unknown concentration of elemental mercury gas and an unknown concentration of oxidized mercury gas;
   deliver the gas sample including the unknown concentration of elemental mercury gas and the unknown concentration of oxidized mercury gas along the first channel to the detector, the mercury monitoring system further comprising:
   an analyzer configured to verify whether the detector detects that the gas sample received on the first channel includes a concentration of elemental mercury gas substantially equal to the known concentration of elemental mercury gas received from the mixing chamber.

31. A mercury monitoring system as in claim 30, wherein the analyzer is configured to determine a correction factor for adjusting future measurement readings provided by the detector when sampling on the first channel if the detector does not detect that the gas sample received on the first channel has a concentration of elemental mercury substantially equal to the known concentration of elemental mercury gas received by the mixing chamber.

32. A mercury monitoring system as in claim 19, wherein the controller is configured to:
   control a flow rate of delivering an oxidizing component to the mixing chamber so that the mixing chamber produces the gas sample to have different concentrations of oxidized mercury gas over a test duration.

33. A mercury monitoring system as in claim 32 further comprising:
   an analyzer configured to initiate operation of the detector at multiple sample times during the test duration to test an ability of the converter to convert the different concentrations of oxidized mercury in the gas sample into elemental mercury.

34. A computer program product having a computer-readable medium including computer program logic stored thereon that, when performed on a controller of a mercury monitoring system, causes the controller to:
   operate a subsystem of the mercury monitoring system to produce a gas sample for calibrating the mercury monitoring system;
   initiate application of a first mode of the mercury monitoring system for delivering the gas sample on a first channel through a converter to a detector operable to measure concentrations of elemental mercury gas in the gas sample, the converter operable to convert oxidized mercury in the gas sample into elemental mercury gas; and
   initiating application of a second mode of the mercury monitoring system for delivering the gas sample to the detector via a second channel that bypasses the converter.

\* \* \* \* \*